US008173434B2

(12) United States Patent
Fan et al.

(10) Patent No.: US 8,173,434 B2
(45) Date of Patent: May 8, 2012

(54) PCAN065 ANTIBODY COMPOSITIONS AND METHODS OF USE

(75) Inventors: Rong A. Fan, Redwood City, CA (US); Kirstin L. Krall, San Jose, CA (US)

(73) Assignee: Diadexus, Inc., South San Francisco, CA (US)

( * ) Notice: Subject to any disclaimer, the term of this patent is extended or adjusted under 35 U.S.C. 154(b) by 0 days.

(21) Appl. No.: 12/904,709

(22) Filed: Oct. 14, 2010

(65) Prior Publication Data
US 2011/0159516 A1   Jun. 30, 2011

Related U.S. Application Data

(63) Continuation of application No. 11/696,442, filed on Apr. 4, 2007, now abandoned.

(60) Provisional application No. 60/789,360, filed on Apr. 4, 2006.

(51) Int. Cl.
G01N 33/48 (2006.01)

(52) U.S. Cl. .......................................... 436/64
(58) Field of Classification Search ...................... 436/64
See application file for complete search history.

(56) References Cited

U.S. PATENT DOCUMENTS

| 5,610,021 | A  | 3/1997  | Rueger et al. |
| 5,994,102 | A  | 11/1999 | Hudson et al. ............... 435/69.4 |
| 6,107,476 | A  | 8/2000  | Erlander et al. ........... 536/23.51 |
| 6,465,181 | B2 | 10/2002 | Billing-Medel et al. .......... 435/6 |
| 6,500,638 | B2 | 12/2002 | Hudson et al. ............... 435/69.1 |
| 6,673,549 | B1 | 1/2004  | Furness et al. .................... 435/6 |
| 6,974,667 | B2 | 12/2005 | Horne et al. ...................... 435/6 |
| 7,141,661 | B2 | 11/2006 | Eling et al. ................... 536/23.2 |
| 7,154,221 | B2 | 12/2006 | Son et al. ....................... 313/582 |
| 7,171,311 | B2 | 1/2007  | Dai et al. ......................... 702/19 |
| 7,189,507 | B2 | 3/2007  | Mack et al. ....................... 435/6 |
| 7,282,351 | B2 | 10/2007 | Hudson et al. ............... 435/69.1 |
| 7,321,830 | B2 | 1/2008  | Munger et al. .................. 702/19 |
| 7,435,589 | B2 | 10/2008 | Mack et al. .................... 435/325 |
| 2001/0010908 | A1 | 8/2001  | Billing-Medel et al. .......... 435/6 |
| 2002/0048784 | A1 | 4/2002  | Hudson et al. ............... 435/69.1 |
| 2002/0086320 | A1 | 7/2002  | Billing-Medel et al. .......... 435/6 |
| 2002/0102531 | A1 | 8/2002  | Horrigan ........................... 435/4 |
| 2002/0102532 | A1 | 8/2002  | Augustus ........................... 435/4 |
| 2002/0110821 | A1 | 8/2002  | Ebner ................................ 435/6 |
| 2002/0115057 | A1 | 8/2002  | Young ................................ 435/4 |
| 2002/0115085 | A1 | 8/2002  | Ebner ................................ 435/6 |
| 2002/0142981 | A1 | 10/2002 | Horne et al. ................. 514/44 R |
| 2002/0150877 | A1 | 10/2002 | Augustus ........................... 435/4 |
| 2002/0160382 | A1 | 10/2002 | Lasek et al. ....................... 435/6 |
| 2002/0165180 | A1 | 11/2002 | Weaver ....................... 514/44 R |
| 2003/0059431 | A1 | 3/2003  | Hudson et al. ............. 435/145.1 |
| 2003/0108871 | A1 | 6/2003  | Kaser ................................ 435/6 |
| 2003/0108963 | A1 | 6/2003  | Schlegel et al. .............. 435/7.23 |
| 2003/0124579 | A1 | 7/2003  | Mack et al. ....................... 435/6 |
| 2003/0134280 | A1 | 7/2003  | Munger et al. .................... 435/6 |
| 2003/0134324 | A1 | 7/2003  | Munger et al. ................. 435/7.1 |
| 2003/0165839 | A1 | 9/2003  | Young et al. ...................... 435/6 |
| 2003/0166903 | A1 | 9/2003  | Astromoff et al. ........... 536/23.2 |
| 2003/0232350 | A1 | 12/2003 | Afar et al. ......................... 435/6 |
| 2004/0005563 | A1 | 1/2004  | Mack et al. ....................... 435/6 |
| 2004/0029770 | A1 | 2/2004  | Eling et al. ........................ 514/1 |
| 2004/0053325 | A1 | 3/2004  | Breit et al. ..................... 435/7.1 |
| 2004/0058340 | A1 | 3/2004  | Dai et al. .......................... 435/6 |
| 2004/0076955 | A1 | 4/2004  | Mack et al. ....................... 435/6 |
| 2004/0110197 | A1 | 6/2004  | Skinner et al. .................... 435/6 |
| 2004/0115625 | A1 | 6/2004  | Ebner ................................ 435/6 |
| 2005/0064454 | A1 | 3/2005  | Young et al. ...................... 435/6 |
| 2005/0191673 | A1 | 9/2005  | Schlegel et al. ................... 435/6 |
| 2005/0233374 | A1 | 10/2005 | Billing-Medel et al. .......... 435/6 |
| 2006/0188889 | A1 | 8/2006  | Burgess et al. ................... 435/6 |
| 2006/0247193 | A1 | 11/2006 | Taira et al. .................. 514/44 A |
| 2006/0263774 | A1 | 11/2006 | Clark et al. ....................... 435/6 |
| 2007/0042360 | A1 | 2/2007  | Afar et al. ......................... 435/6 |
| 2007/0059708 | A1 | 3/2007  | Corfe et al. ....................... 435/6 |
| 2007/0059748 | A1 | 3/2007  | Afar et al. ......................... 435/6 |
| 2007/0154928 | A1 | 7/2007  | Mack et al. ....................... 435/6 |

(Continued)

FOREIGN PATENT DOCUMENTS

| JP | 7-250688 | 10/1995 |
| JP | 7-258293 | 10/1995 |
| KR | 10-2004-0079266 | 9/2004 |
| WO | WO 97/00958 | 1/1997 |
| WO | WO 03/058021 A2 | 7/2003 |
| WO | WO 2004/060270 A2 | 7/2004 |
| WO | WO 2004/076614 A2 | 9/2004 |
| WO | WO 2004/108899 A2 | 12/2004 |

OTHER PUBLICATIONS

Agarwal et al. "Macrophage Inhibitory Cytokine 1 Mediates a p53-dependent Protective Arrest in S Phase in Response to Starvation for DNA Precursors" Proceedings of the National Academy of Science USA 2006 vol. 103(44): 16278-16283.

Albertoni et al. "Anoxia Induces Macrophage Inhibitory Cytokine-1 (MIC-1) in Glioblastoma Cells Independently of p53 and HIF-1" Oncogene 2002 vol. 21: 4212-4219.

Appierto et al. "Analysis of Gene Expression Identifies PLAB as a Mediator of the Apoptotic Activity of Fenretinide in Human Ovarian Cancer Cells" Oncogene 2007 vol. 26: 3952-3962.

Baek et al. "Cyclooxygenase Inhibitors Regulate the Expression of a TGF-β Superfamily Member that has Proapoptotic and Antitumorigenic Activities" Molecular Pharmacology 2001 vol. 59(4): 901-908.

(Continued)

Primary Examiner — Misook Yu
Assistant Examiner — Brad Duffy
(74) Attorney, Agent, or Firm — Licata & Tyrell P.C.; Keith R. McCollum

(57) ABSTRACT

The invention provides isolated anti-PCan065 antibodies that bind to PCan065. The invention also encompasses compositions comprising an anti-PCan065 antibody and a carrier. These compositions can be provided in an article of manufacture or a kit. Another aspect of the invention is an isolated nucleic acid encoding an anti-PCan065 antibody, as well as an expression vector comprising the isolated nucleic acid. Also provided are cells that produce the anti-PCan065 antibodies. The invention encompasses a method of producing the anti-PCan065 antibodies. Other aspects of the invention are a method of killing an PCan065-expressing cancer cell, comprising contacting the cancer cell with an anti-PCan065 antibody and a method of alleviating or treating an PCan065-expressing cancer in a mammal, comprising administering a therapeutically effective amount of the anti-PCan065 antibody to the mammal.

14 Claims, 2 Drawing Sheets

U.S. PATENT DOCUMENTS

| | | | |
|---|---|---|---|
| 2007/0161016 A1 | 7/2007 | Afar et al. | 435/6 |
| 2007/0166310 A1 | 7/2007 | Hudson et al. | 424/145.1 |
| 2007/0180543 A1 | 8/2007 | Eling et al. | 800/14 |
| 2007/0224201 A1 | 9/2007 | Wu et al. | 424/155.1 |
| 2008/0050379 A1 | 2/2008 | Young et al. | 424/138.1 |
| 2008/0194043 A1 | 8/2008 | Astle et al. | 435/501 |
| 2008/0233585 A1 | 9/2008 | Burgess et al. | 435/6 |
| 2009/0098131 A1 | 4/2009 | Clark et al. | 424/139.1 |
| 2009/0286313 A1 | 11/2009 | Eling et al. | 435/325 |
| 2009/0291889 A1 | 11/2009 | Breit et al. | 514/12 |

OTHER PUBLICATIONS

Baek et al. "Expression of NAG-1, a Transforming Growth Factor-β Superfamily Member, by Troglitazone Requires the Early Growth Response Gene *EGR-1*" The Journal of Biological Chemistry 2004 vol. 279(8): 6883-6892.

Baek et al. "Molecular Cloning and Characterization of Human Nonsteroidal Anti-Inflammatory Drug-Activated Gene Promoter" The Journal of Biological Chemistry 2001 vol. 276(36): 33384-33392.

Baek et al. "Resveratrol Enhances the Expression of Non-Steroidal Anti-Inflammatory Drug-Activated Gene (NAG-1) by Increasing the Expression of p53" Carcinogenesis 2002 vol. 23(3): 425-434.

Bauskin et al. "Role of Macrophage Inhibitory Cytokine-1 in Tumorigenesis and Diagnosis of Cancer" Cancer Research 2006 vol. 66(10): 4983-4986.

Bauskin et al. "The Propeptide of Macrophage Inhibitory Cytokine (MIC-1), a TGF-β Superfamily Member, Acts as a Quality Control Determinant for Correctly Folded MIC-1" The EMBO Journal 2000 vol. 19(10): 2212-2220.

Bootcov et al. "MIC-1, a Novel Macrophage Inhibitory Cytokine, is a Divergent Member of the TGF-β Superfamily" Proceedings of the National Academy of Science USA 1997 vol. 94: 11514-11519.

Böttner et al. "Characterization of the Rat, Mouse, and Human Genes of Growth/Differentiation Factor-15/Macrophage Inhibiting Cytokine-1 (GDF-15/MIC-1)" Gene 1999 vol. 237: 105-111.

Brown et al. "Antibody-Based Approach to High-Volume Genotyping for MIC-1 Polymorphism" BioTechniques 2002 vol. 33(1): 118-126.

Brown et al. "Concentration in Plasma of Macrophage Inhibitory Cytokine-1 and Risk of Cardiovascular Events in Women: A Nested Case-Control Study" The Lancet 2002 vol. 359: 2159-2163.

Brown et al. "MIC-1 Serum Level and Genotype: Associations with Progress and Prognosis of Colorectal Carcinoma" Clinical Cancer Research 2003 vol. 9: 2641-2650.

Buckhaults et al. "Secreted and Cell Surfaces Genes Expressed in Benign and Malignant Colorectal Tumors" Cancer Research 2001 vol. 61: 6996-7001.

Cheung et al. "Protein Profiling of Microdissected Prostate Tissue Links Growth Differentiation Factor 15 to Prostate Carcinogenesis" Cancer Research 2004 vol. 64: 5929-5933.

Fairlie et al. "Epitope Mapping of the Transforming Growth Factor-β Superfamily Protein, Macrophage Inhibitory Cytokine-1 (MIC-1): Identification of at Least Five Distinct Epitope Specificities" Biochemistry 2001 vol. 40: 65-73.

Fairlie et al. "Expression of a TGF-β Superfamily Protein, Macrophage Inhibitory Cytokine-1, in the Yeast *Pichia pastoris*" Gene 2000 vol. 254: 67-76.

Fairlie et al. "MIC-1 is a Novel TGF-β Superfamily Cytokine Associated with Macrophage Activation" Journal of Leukocyte Biology 1999 vol. 65: 2-5.

Fairlie et al. "The Propeptide of the Transforming Growth Factor-β Superfamily Member, Macrophage Inhibitory Cytokine-1 (MIC-1), is a Multifunctional Domain that can Facilitate Protein Folding and Secretion" The Journal of Biological Chemistry 2001 vol. 276(20) : 16911-16918.

Golkar et al. "Resveratrol Inhibits Pancreatic Cancer Cell Proliferation Through Transcriptional Induction of Macrophage Inhibitory Cytokine-1" Journal of Surgical Research 2007 vol. 138: 163-169.

Graichen et al. "Autocrine Human Growth Hormone Inhibits Placental Transforming Growth Factor-β Gene Transcription to Prevent Apoptosis and Allow Cell Cycle Progression of Human Mammary Carcinoma Cells" The Journal of Biological Chemistry 2002 vol. 277(29): 26662-26672.

Hayes et al. "Macrophage Inhibitory Cytokine-1 H6D Polymorphism, Prostate Cancer Risk, and Survival" Cancer Epidemiology, Biomarkers & Prevention 2006 vol. 15(6): 1223-1225.

Hromas et al. "PLAB, a Novel Placental Bone Morphogenetic Protein" Biochimica et Biophysica Acta 1997 vol. 1354: 40-44.

Iczkowski, K.A. and Pantazis, C.G. "Overexpression of NSAID-Activated Gene Product in Prostate Cancer" International Journal of Surgical Pathology 2003 vol. 11(3): 159-166.

Kadara et al. "Induction of GDF-15/NAG-1/MIC-1 in Human Lung Carcinoma Cells by Retinoid-Related Molecules and Assessment of Its Role in Apoptosis" Cancer Biology & Therapy 2006 vol. 5(5): 518-522.

Keelan et al. "Macrophage Inhibitory Cytokine 1 in Fetal Membranes and Amniotic Fluid from Pregnancies With and Without Preterm Labour and Premature Rupture of Membranes" Molecular Human Reproduction 2003 vol. 9(9): 535-540.

Kim et al. "The Conventional Nonsteroidal Anti-Inflammatory Drug Sulindac Sulfide Arrests Ovarian Cancer Cell Growth Via the Expression of *NAG-1/MIC-1/GDF-15*" Molecular Cancer Therapeutics 2005 vol. 4(3): 487-493.

Kim et al. "Expression of Non-Steroidal Anti-Inflammatory Drug-Activated Gene-1 in Human Nasal Mucosa and Cultured Nasal Epithelial Cells: A Preliminary Investigation" Acta Otolaryngol 2003 vol. 123: 857-861.

Koopmann et al. "Serum Macrophage Inhibitory Cytokine 1 as a Marker of Pancreatic and Other Preiampullary Cancers" Clinical Cancer Research 2004 vol. 10: 2386-2392.

Koopmann "Serum Markers in Patients with Resectable Pancreatic Adenocarcinoma: Macrophage Inhibitory Cytokine 1 Versus CA19-9" Clinical Cancer Research 2006 vol. 12(2): 442-446.

Lawton et al. "Identification of a Novel Member of the TGF-beta Superfamily Highly Expressed in Human Placenta" Gene 1997 vol. 203: 17-26.

Lee et al. "Indole-3-Carbinol and 3,3'-Diindolylmethane Induce Expression of NAG-1 in a p53-Independent Manner" Biochemical and Biophysical Research Communications 2005 vol. 328: 63-69.

Li et al. "Placental Transforming Growth Factor-β is a Downstream Mediator of the Growth Arrest and Apoptotic Response of Tumor Cells to DNA Damage and p53 Overexpression" The Journal of Biological Chemistry 2000 vol. 275(26): 20127-20135.

Lindmark et al. "H6D Polymorphism in Macrophage-Inhibitory Cytokine-1 Gene Associated with Prostate Cancer" Journal of the National Cancer Institute 2004 vol. 96(16): 1248-1254.

Liu et al. "Macrophage Inhibitory Cytokine 1 Reduces Cell Adhesion and Induces Apoptosis in Prostate Cancer Cells" Cancer Research 2003 vol. 63: 5034-5040.

Mammalian Gene Collection (MGC) Program Team "Generation and Initial Analysis of More than 15,000 Full-Length Human and Mouse cDNA Sequences" Proceedings of the National Academy of Science USA 2002 vol. 99(26): 16899-16903.

Martinez et al. "Drug-Induced Expression of Nonsteroidal Anti-Inflammatory Drug-Activated Gene/Macrophage Inhibitory Cytokine-1/Prostate-Derived Factor, a Putative Tumor Suppressor, Inhibits Tumor Growth" The Journal of Pharmacology and Experimental Therapeutics 2006 vol. 318(2): 899-906.

Moore et al. "The Transforming Growth Factor-β Superfamily Cytokine Macrophage Inhibitory Cytokine-1 is Present in High Concentrations in the Serum of Pregnant Women" The Journal of Clinical Endocrinology & Metabolism 2000 vol. 85(12): 4781-4788.

Paralkar et al. "Cloning and Characterization of a Novel Member of the Transforming Growth Factor-β/Bone Morphogenetic Protein Family" The Journal of Biological Chemistry 1998 vol. 273(22): 13760-13767.

Selander et al. "Serum Macrophage Inhibitory Cytokine-1 Concentrations Correlate with the Presence of Prostate Cancer Bone Metastases" Cancer Epidemiology, Biomarkers & Prevention 2007 vol. 16(3): 532-537.

Shim, M. and Eling, T.E. "Protein Kinase C-Dependent Regulation of NAG-1/Placental Bone Morphogenic Protein/MIC-1 Expression in LNCaP Prostate Carcinoma Cells" The Journal of Biological Chemistry 2005 vol. 280(19): 18636-18642.

Strelau et al. "Growth/Differentiation Factor 15/Macrophage Inhibitory Cytokine-1 Is a Novel Trophic Factor for Midbrain Dopaminergic Neurons In Vivo" The Journal of Neuroscience 2000 vol. 20(23): 8597-8603.

Subramaniam et al. "Growth Differentiation Factor-15 Prevents Low Potassium-Induced Cell Death of Cerebellar Granule Neurons by Differential Regulation of Akt and ERK Pathways" The Journal of Biological Chemistry 2003 vol. 278(11): 8904-8912.

Tong et al. "Serum Concentrations of Macrophage Inhibitory Cytokine 1 (MIC 1) as a Predictor of Miscarriage" The Lancet 2004 vol. 363: 129-130.

Wollmann et al. "The Macrophage Inhibitory Cytokine Integrates AKT/PKB and MAP Kinase Signaling Pathways in Breast Cancer Cells" Carcinogenesis 2005 vol. 26(5): 900-907.

Wong et al. "A Novel p53 Transcriptional Repressor Element (p53TRE) and the Asymmetrical Contribution of Two p53 Binding Sites Modulate the Response of the Placental Transforming Growth Factor-β Promoter to p53" The Journal of Biological Chemistry 2002 vol. 277(29): 26699-26707.

Yokoyama-Kobayashi et al. "Human cDNA Encoding a Novel TGF-β Superfamily Protein Highly Expressed in Placenta" Journal of Biochemistry 1997 vol. 122: 622-626.

Zimmers et al. "Growth Differentiation Factor-15: Induction in Liver Injury Through p53 and Tumor Necrosis Factor-Independent Mechanisms" Journal of Surgical Research 2006 vol. 130: 45-51.

NCBI Reference Sequence NM_004864.2, Locus NM_004862 PRI Jun. 6, 2010.

NCBI Reference Sequence NP_004855.2, Locus NP_004855 PRI Jun. 6, 2010.

Goat Anti-MIC-1/GDF-15 Polycolonal Antibody, Catalogue No. AF957, from R&D Systems (Minneapolis, MN), 2004.

Rabbit Anti-MIC-1/GDF-15 Polycolonal Antibody, Catalogue No. PAB-10692, from Orbigen (San Diego, CA), 2010.

George et al. (Circulation. 1998; 97:900-906).

Jones (Pharmacogenomics Journal, 1:126-134, 2001).

Tosatto et al. (Current Pharmaceutical Design, 12:2067-2086, 2006).

Skolnick et al. (Trends in Biotechnology 2000; 18:34-39).

Tchou et al. (Biom., iFirst :1-5, 2009).

Welsh et al. (PNAS, 100(6)3410-3415,2003).

PCAN065 ANTIBODY COMPOSITIONS AND METHODS OF USE

This patent application is a continuation of U.S. Ser. No. 11/696,442 filed Apr. 4, 2007 now abandoned, which claims the benefit of priority from U.S. Provisional Application Ser. No. 60/789,360, filed Apr. 4, 2006, teachings of which are herein incorporated by reference in their entireties.

FIELD OF THE INVENTION

The present invention relates to anti-PCan065 antibody compositions and methods of detecting ovarian, breast, colon, prostate, pancreatic or lung cancer and killing PCan065-expressing ovarian, breast, colon, prostate, pancreatic or lung cancer cells.

BACKGROUND OF THE INVENTION

Ovarian Cancer

Cancer of the ovaries is the fourth-most common cause of cancer death in women in the United States, with more than 23,000 new cases and roughly 14,000 deaths predicted for the year 2001. Shridhar, V. et al., *Cancer Res.* 61(15): 5895-904 (2001); Memarzadeh, S. & Berek, J. S., *J. Reprod. Med.* 46(7): 621-29 (2001). The American Cancer Society (ACS) estimates that there will be about 25,580 new cases of ovarian cancer in 2004 and ovarian cancer will cause about 16,090 deaths in the United States. ACS Website: cancer with the extension .org of the world wide web. More women die annually from ovarian cancer than from all other gynecologic malignancies combined. The incidence of ovarian cancer in the US is estimated to 14.2 per 100,000 women per year and 9 women per 100,000 die every year from ovarian cancer. In 2004, approximately 70-75% of new diagnoses will be stage III and IV carcinoma with a predicted 5-year survival of ~15%. Jemal et al., Annual Report to the Nation on the Status of Cancer, 1975-2001, with a Special Feature Regarding Survival. Cancer 2004; 101: 3-27. The incidence of ovarian cancer is of serious concern worldwide, with an estimated 191,000 new cases predicted annually. Runnebaum, I. B. & Stickeler, E., *J. Cancer Res. Clin. Oncol.* 127(2): 73-79 (2001). Unfortunately, women with ovarian cancer are typically asymptomatic until the disease has metastasized. Because effective screening for ovarian cancer is not available, roughly 70% of women diagnosed have an advanced stage of the cancer with a five-year survival rate of ~25-30%. Memarzadeh, S. & Berek, J. S., supra; Nunns, D. et al., *Obstet. Gynecol. Surv.* 55(12): 746-51. Conversely, women diagnosed with early stage ovarian cancer enjoy considerably higher survival rates. Werness, B. A. & Eltabbakh, G. H., *Int'l. J. Gynecol. Pathol.* 20(1): 48-63 (2001). Although our understanding of the etiology of ovarian cancer is incomplete, the results of extensive research in this area point to a combination of age, genetics, reproductive, and dietary/environmental factors. Age is a key risk factor in the development of ovarian cancer: while the risk for developing ovarian cancer before the age of 30 is slim, the incidence of ovarian cancer rises linearly between ages 30 to 50, increasing at a slower rate thereafter, with the highest incidence being among septagenarian women. Jeanne M. Schilder et al., *Hereditary Ovarian Cancer: Clinical Syndromes and Management*, in *Ovarian Cancer* 182 (Stephen C. Rubin & Gregory P. Sutton eds., 2d ed. 2001).

With respect to genetic factors, a family history of ovarian cancer is the most significant risk factor in the development of the disease, with that risk depending on the number of affected family members, the degree of their relationship to the woman, and which particular first degree relatives are affected by the disease. Id. Mutations in several genes have been associated with ovarian cancer, including BRCA1 and BRCA2, both of which play a key role in the development of breast cancer, as well as hMSH2 and hMLH1, both of which are associated with hereditary non-polyposis colon cancer. Katherine Y. Look, *Epidemiology, Etiology, and Screening of Ovarian Cancer*, in *Ovarian Cancer* 169, 171-73 (Stephen C. Rubin & Gregory P. Sutton eds., 2d ed. 2001). BRCA1, located on chromosome 17, and BRCA2, located on chromosome 13, are tumor suppressor genes implicated in DNA repair; mutations in these genes are linked to roughly 10% of ovarian cancers. Id. at 171-72; Schilder et al., supra at 185-86. hMSH2 and hMLH1 are associated with DNA mismatch repair, and are located on chromosomes 2 and 3, respectively; it has been reported that roughly 3% of hereditary ovarian carcinomas are due to mutations in these genes. Look, supra at 173; Schilder et al., supra at 184, 188-89.

Reproductive factors have also been associated with an increased or reduced risk of ovarian cancer. Late menopause, nulliparity, and early age at menarche have all been linked with an elevated risk of ovarian cancer. Schilder et al., supra at 182. One theory hypothesizes that these factors increase the number of ovulatory cycles over the course of a woman's life, leading to "incessant ovulation," which is thought to be the primary cause of mutations to the ovarian epithelium. Id.; Laura J. Havrilesky & Andrew Berchuck, *Molecular Alterations in Sporadic Ovarian Cancer*, in *Ovarian Cancer* 25 (Stephen C. Rubin & Gregory P. Sutton eds., 2d ed. 2001). The mutations may be explained by the fact that ovulation results in the destruction and repair of that epithelium, necessitating increased cell division, thereby increasing the possibility that an undetected mutation will occur. Id. Support for this theory may be found in the fact pregnancy, lactation, and the use of oral contraceptives, all of which suppress ovulation, confer a protective effect with respect to developing ovarian cancer. Id.

Among dietary/environmental factors, there would appear to be an association between high intake of animal fat or red meat and ovarian cancer, while the antioxidant Vitamin A, which prevents free radical formation and also assists in maintaining normal cellular differentiation, may offer a protective effect. Look, supra at 169. Reports have also associated asbestos and hydrous magnesium trisilicate (talc), the latter of which may be present in diaphragms and sanitary napkins. Id. at 169-70.

Current screening procedures for ovarian cancer, while of some utility, are quite limited in their diagnostic ability, a problem that is particularly acute at early stages of cancer progression when the disease is typically asymptomatic yet is most readily treated. Walter J. Burdette, *Cancer: Etiology, Diagnosis, and Treatment* 166 (1998); Memarzadeh & Berek, supra; Runnebaum & Stickeler, supra; Werness & Eltabbakh, supra. 0Commonly used screening tests include biannual rectovaginal pelvic examination, radioimmunoassay to detect the CA-125 serum tumor marker, and transvaginal ultrasonography. Burdette, supra at 166. Currently, CA-125 is the only clinically approved serum marker for use in ovarian cancer. CA-125 is found elevated in the majority of serous cancers, but is elevated in only half of those women with early stage disease. The major clinical application of CA125 is in monitoring treatment success or detection of recurrence in women undergoing treatment for ovarian cancer. Markman M. *The Oncologist;* 2: 6-9 (1997). The use of CA125 as a screening marker is limited because it is frequently elevated in women with benign diseases such as endometriosis. Hence, there is a critical need for novel serum markers that are more sensitive and specific for the detection of ovarian cancer when used alone, or in combination with CA125. Bast R C. Et al., *Early Detection of Ovarian Cancer: Promise and Reality* in *Ovarian Cancer. Cancer Research and Treatment* Vol 107 (Stack M S, Fishman, D A, eds., 2001).

Pelvic examination has failed to yield adequate numbers of early diagnoses, and the other methods are not sufficiently accurate. Id. One study reported that only 15% of patients who suffered from ovarian cancer were diagnosed with the disease at the time of their pelvic examination. Look, supra at 174. Moreover, the CA-125 test is prone to giving false positives in pre-menopausal women and has been reported to be of low predictive value in post-menopausal women. Id. at 174-75. Although transvaginal ultrasonography is now the preferred procedure for screening for ovarian cancer, it is unable to distinguish reliably between benign and malignant tumors, and also cannot locate primary peritoneal malignancies or ovarian cancer if the ovary size is normal. Schilder et al., supra at 194-95. While genetic testing for mutations of the BRCA1, BRCA2, hMSH2, and hMLH1 genes is now available, these tests may be too costly for some patients and may also yield false negative or indeterminate results. Schilder et al., supra at 191-94.

Additionally, current efforts focus on the identification of panels of biomarkers that can be used in combination. Bast R C Jr., J Clin Oncol 2003; 21: 200-205. Currently, other markers being evaluated as potential ovarian serum markers which may serve as members of a multi-marker panel to improve detection of ovarian cancer are HE4; mesothelin; kallikrein 5, 8, 10 and 11; and prostasin. Urban et al. Ovarian cancer screening Hematol Oncol Clin North Am. 2003 August; 17(4):989-1005; Hellstrom et al. The HE4 (WFDC2) protein is a biomarker for ovarian carcinoma, Cancer Res. 2003 Jul. 1; 63(13):3695-700; Ordonez, Application of mesothelin immunostaining in tumor diagnosis, Am J Surg Pathol. 2003 November; 27(11):1418-28; Diamandis E P et al., Cancer Research 2002; 62: 295-300; Yousef G M et al., Cancer Research 2003; 63: 3958-3965; Kishi T et al., Cancer Research 2003; 63: 2771-2774; Luo L Y et al., Cancer Research 2003; 63: 807-811; Mok S C et al., J Natl Cancer Inst 2001; 93 (19): 1437-1439.

The staging of ovarian cancer, which is accomplished through surgical exploration, is crucial in determining the course of treatment and management of the disease. *AJCC Cancer Staging Handbook* 187 (Irvin D. Fleming et al. eds., 5th ed. 1998); Burdette, supra at 170; Memarzadeh & Berek, supra; Shridhar et al., supra. Staging is performed by reference to the classification system developed by the International Federation of Gynecology and Obstetrics. David H. Moore, *Primary Surgical Management of Early Epithelial Ovarian Carcinoma*, in *Ovarian Cancer* 203 (Stephen C. Rubin & Gregory P. Sutton eds., 2d ed. 2001); Fleming et al. eds., supra at 188. Stage I ovarian cancer is characterized by tumor growth that is limited to the ovaries and is comprised of three substages. Id. In substage IA, tumor growth is limited to one ovary, there is no tumor on the external surface of the ovary, the ovarian capsule is intact, and no malignant cells are present in ascites or peritoneal washings. Id. Substage IB is identical to A1, except that tumor growth is limited to both ovaries. Id. Substage IC refers to the presence of tumor growth limited to one or both ovaries, and also includes one or more of the following characteristics: capsule rupture, tumor growth on the surface of one or both ovaries, and malignant cells present in ascites or peritoneal washings. Id.

Stage II ovarian cancer refers to tumor growth involving one or both ovaries, along with pelvic extension. Id. Substage IIA involves extension and/or implants on the uterus and/or fallopian tubes, with no malignant cells in the ascites or peritoneal washings, while substage IIB involves extension into other pelvic organs and tissues, again with no malignant cells in the ascites or peritoneal washings. Id. Substage IIC involves pelvic extension as in IIA or IIB, but with malignant cells in the ascites or peritoneal washings. Id.

Stage III ovarian cancer involves tumor growth in one or both ovaries, with peritoneal metastasis beyond the pelvis confirmed by microscope and/or metastasis in the regional lymph nodes. Id. Substage IIIA is characterized by microscopic peritoneal metastasis outside the pelvis, with substage IIIB involving macroscopic peritoneal metastasis outside the pelvis 2 cm or less in greatest dimension. Id. Substage IIIC is identical to IIIB, except that the metastasis is greater than 2 cm in greatest dimension and may include regional lymph node metastasis. Id. Lastly, Stage IV refers to the presence distant metastasis, excluding peritoneal metastasis. Id.

While surgical staging is currently the benchmark for assessing the management and treatment of ovarian cancer, it suffers from considerable drawbacks, including the invasiveness of the procedure, the potential for complications, as well as the potential for inaccuracy. Moore, supra at 206-208, 213. In view of these limitations, attention has turned to developing alternative staging methodologies through understanding differential gene expression in various stages of ovarian cancer and by obtaining various biomarkers to help better assess the progression of the disease. Vartiainen, J. et al., *Int'l J. Cancer,* 95(5): 313-16 (2001); Shridhar et al. supra; Baekelandt, M. et al., *J. Clin. Oncol.* 18(22): 3775-81.

The treatment of ovarian cancer typically involves a multiprong attack, with surgical intervention serving as the foundation of treatment. Dennis S. Chi & William J. Hoskins, *Primary Surgical Management of Advanced Epithelial Ovarian Cancer*, in *Ovarian Cancer* 241 (Stephen C. Rubin & Gregory P. Sutton eds., 2d ed. 2001). For example, in the case of epithelial ovarian cancer, which accounts for ~90% of cases of ovarian cancer, treatment typically consists of: (1) cytoreductive surgery, including total abdominal hysterectomy, bilateral salpingo-oophorectomy, omentectomy, and lymphadenectomy, followed by (2) adjuvant chemotherapy with paclitaxel and either cisplatin or carboplatin. Eltabbakh, G. H. & Awtrey, C. S., *Expert Op. Pharmacother.* 2(10): 109-24. Despite a clinical response rate of 80% to the adjuvant therapy, most patients experience tumor recurrence within three years of treatment. Id. Certain patients may undergo a second cytoreductive surgery and/or second-line chemotherapy. Memarzadeh & Berek, supra.

From the foregoing, it is clear that procedures used for detecting, diagnosing, monitoring, staging, prognosticating, and preventing the recurrence of ovarian cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop ovarian cancer, for diagnosing ovarian cancer, for monitoring the progression of the disease, for staging the ovarian cancer, for determining whether the ovarian cancer has metastasized, and for imaging the ovarian cancer. There is also a need for better treatment of ovarian cancer.

Angiogenesis in Cancer

Growth and metastasis of solid tumors are also dependent on angiogenesis. Folkman, J., 1986, *Cancer Research*, 46, 467-473; Folkman, J., 1989, *Journal of the National Cancer Institute*, 82, 4-6. It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone. Weidner, N., et al., 1991, *The New England Journal of Medicine*, 324(1), 1-8.

Angiogenesis, defined as the growth or sprouting of new blood vessels from existing vessels, is a complex process that primarily occurs during embryonic development. The process is distinct from vasculogenesis, in that the new endothelial cells lining the vessel arise from proliferation of existing cells, rather than differentiating from stem cells. The process is invasive and dependent upon proteolysis of the extracellular matrix (ECM), migration of new endothelial cells, and synthesis of new matrix components. Angiogenesis occurs during embryogenic development of the circulatory system; however, in adult humans, angiogenesis only occurs as a response to a pathological condition (except during the reproductive cycle in women).

Under normal physiological conditions in adults, angiogenesis takes place only in very restricted situations such as hair growth and wounding healing. Auerbach, W. and Auerbach, R., 1994, *Pharmacol Ther.* 63(3):265-3 11; Ribatti et al., 1991, *Haematologica* 76(4):3 11-20; Risau, 1997, *Nature* 386(6626):67 1-4. Angiogenesis progresses by a stimulus which results in the formation of a migrating column of endothelial cells. Proteolytic activity is focused at the advancing tip of this "vascular sprout", which breaks down the ECM sufficiently to permit the column of cells to infiltrate and migrate. Behind the advancing front, the endothelial cells differentiate and begin to adhere to each other, thus forming a new basement membrane. The cells then cease proliferation and finally define a lumen for the new arteriole or capillary.

Unregulated angiogenesis has gradually been recognized to be responsible for a wide range of disorders, including, but not limited to, cancer, cardiovascular disease, rheumatoid arthritis, psoriasis and diabetic retinopathy. Folkman, 1995, *Nat Med* 1(1):27-31; Isner, 1999, *Circulation* 99(13): 1653-5; Koch, 1998, *Arthritis Rheum* 41(6):951-62; Walsh, 1999, *Rheumatology* (Oxford) 38(2):103-12; Ware and Simons, 1997, *Nat Med* 3(2): 158-64.

Of particular interest is the observation that angiogenesis is required by solid tumors for their growth and metastases. Folkman, 1986 supra; Folkman 1990, *J Natl. Cancer Inst.*, 82(1) 4-6; Folkman, 1992, *Semin Cancer Biol* 3(2):65-71; Zetter, 1998, *Annu Rev Med* 49:407-24. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors Folkman, 1995, supra.

One of the most potent angiogenesis inhibitors is endostatin identified by O'Reilly and Folkman. O'Reilly et al., 1997, *Cell* 88(2):277-85; O'Reilly et al., 1994, *Cell* 79(2):3 15-28. Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII). Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles. Boehm et al., 1997, Nature 390(6658):404-407. The fact that endostatin targets genetically stable endothelial cells and inhibits a variety of solid tumors makes it a very attractive candidate for anticancer therapy. Fidler and Ellis, 1994, *Cell* 79(2):185-8; Gastl et al., 1997, Oncology 54(3):177-84; Hinsbergh et al., 1999, Ann Oncol 10 Suppl 4:60-3. In addition, angiogenesis inhibitors have been shown to be more effective when combined with radiation and chemotherapeutic agents. Klement, 2000, J. Clin Invest, 105(8) R15-24. Browder, 2000, Cancer Res. 6-(7) 1878-86, Arap et al., 1998, Science 279(5349): 377-80; Mauceri et al., 1998, Nature 394(6690):287-91.

As discussed above, each of the methods for diagnosing and staging ovarian, breast, colon, prostate, pancreatic or lung cancer is limited by the technology employed. Accordingly, there is need for sensitive molecular and cellular markers for the detection of ovarian, breast, colon, prostate, pancreatic or lung cancer. There is a need for molecular markers for the accurate staging, including clinical and pathological staging, of ovarian, breast, colon, prostate, pancreatic or lung cancers to optimize treatment methods. In addition, there is a need for sensitive molecular and cellular markers to monitor the progress of cancer treatments, including markers that can detect recurrence of ovarian, breast, colon, prostate, pancreatic or lung cancers following remission.

The present invention provides alternative methods of treating ovarian, breast, colon, prostate, pancreatic or lung cancer that overcome the limitations of conventional therapeutic methods as well as offer additional advantages that will be apparent from the detailed description below.

SUMMARY OF THE INVENTION

This invention is directed to an isolated PCan065 antibody that binds to PCan065 on a mammalian cell. The invention is further directed to an isolated PCan065 antibody that internalizes upon binding to PCan065 on a mammalian cell. The antibody may be a monoclonal antibody. Alternatively, the antibody is an antibody fragment or a chimeric or a humanized antibody. The monoclonal antibody may be produced by a hybridoma selected from the group of hybridomas deposited under American Type Culture Collection comprising PCan065.A10.3.2 and PCan065.B2.2.1, respectively.

The antibody may compete for binding to the same epitope as the epitope bound by the monoclonal antibody produced by a hybridoma selected from the group of hybridomas deposited under the American Type Culture Collection comprising PCan065.A10.3.2 and PCan065.B2.2.1, respectively.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, maytansin, maytansinoids, saporin, gelonin, ricin or calicheamicin.

The mammalian cell may be a cancer cell. Preferably, the anti-PCan065 monoclonal antibody that inhibits the growth of PCan065-expressing cancer cells.

The antibody may be produced in bacteria. Alternatively, the antibody may be a humanized form of an anti-PCan065 antibody produced by a hybridoma selected from the group of hybridomas deposited with the ATCC comprising PCan065.A10.3.2 and PCan065.B2.2.1.

Preferably, the cancer is selected from the group consisting of ovarian, colon, prostate, and lung cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing an PCan065-expressing cancer cell, comprising contacting the cancer cell with the antibodies of this invention, thereby killing the cancer cell. The cancer cell may be selected from the group consisting of ovarian, colon, prostate, and lung cancer cell.

The ovarian, colon, prostate or lung may be metastatic cancer. The breast cancer may be HER-2 negative breast cancer. The invention is also directed to a method of alleviating an PCan065-expressing cancer in a mammal, comprising administering a therapeutically effective amount of the antibodies to the mammal.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat ovarian, breast, colon, prostate, pancreatic or lung cancer.

DETAILED DESCRIPTION OF THE INVENTION

Definitions and General Techniques

Figure 1:
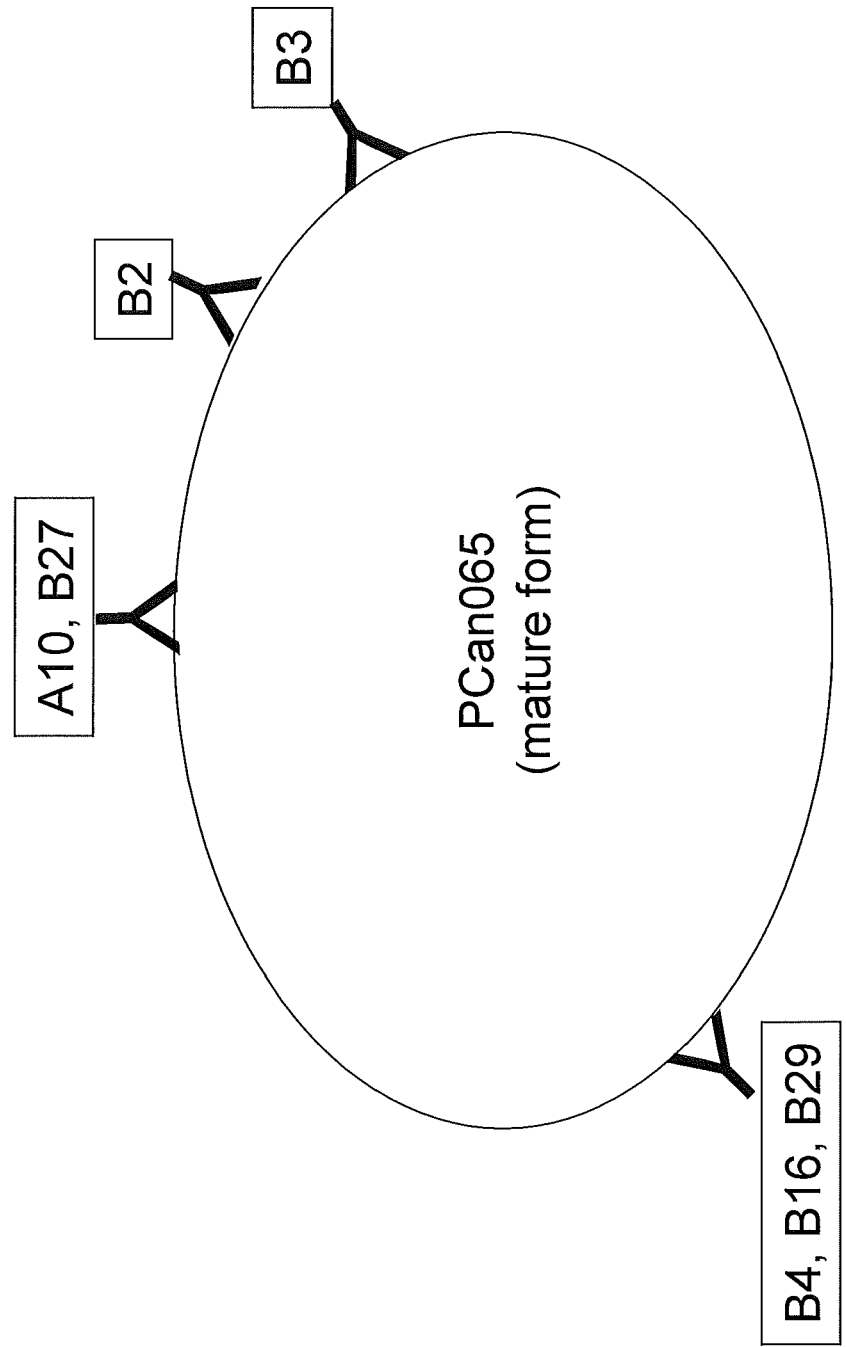
FIG. 1 shows the PCan065 epitope map for anti-PCan065 antibodies.

Human "PCan065" as used herein, refers to a protein of 308 amino acids that is secreted by cells, whose nucleotide and amino acid sequence sequences are disclosed wholly or in part in e.g., WO 96/18730-A1 as Human prostatic growth factor; JP07250688-A as Human TGF-beta superfamily protein; WO 2001/81928-A1 as Human macrophage inhibitory cytokine 1 (MIC-1) wild type and allelic variant protein; WO 2003/058021-A2 as Human apoptosis-associated protein SEQ ID 514; and WO 97/00958-A1 as Human TGF-beta-like cytokine pCL13 and variants dd2, d2, h1, b1, u2, b2, a1, f1; the disclosures of which are hereby expressly incorporated by reference. The 308 amino acid sequence of PCan065 is depicted in SEQ ID NO:5. Amino acids 1-308, 30-308, 35-308, 197-308, 207-308, 208-308 or 211-308 (with or without the N-terminal secretory signal peptide and pre-, pro- and mature forms) of PCan065 are secreted from cells as single molecules, dimers or multi-mers. PCan065 as used herein includes allelic variants and conservative substitution mutants of the protein which have PCan065 biological activity.

PCan065 is related the *Homo sapiens* growth differentiation factor (GDF) family and is identified in the RefSeq database as accessions NM_004864 and NP_004855 (accessible at ncbi with the extension .nlm.nih.gov of the world wide web) and titled "*Homo sapiens* growth differentiation factor 15 (GDF15)". Other synonyms for PCan065 include: prostate differentiation factor (PDF); MIC1; PLAB; macrophage inhibitory cytokine (MIC-1); NAG-1; PTGF-beta (PTGFB); GDF-15; and NSAID (nonsteroidal anti-inflammatory drug)-activated protein 1. The refseq database includes the following summary of PCan065:

> Bone morphogenetic proteins (e.g., BMP5; MIM 112265) are members of the transforming growth factor-beta (see TGFB1; MIM 190180) superfamily and regulate tissue differentiation and maintenance. They are synthesized as precursor molecules that are processed at a dibasic cleavage site to release C-terminal domains containing a characteristic motif of 7 conserved cysteines in the mature protein. [supplied by OMIM]

Many publications have described the identification, characterization, association with disease, and clinical development of PCan065 as a molecular target for disease detection, therapy and vaccination including the following which are hereby incorporated by reference in their entirety.

---

Selander K S, Brown D A, Sequeiros G B, Hunter M, Desmond R, Parpala T, Risteli J, Breit S N, Jukkola-Vuorinen A.
Serum macrophage inhibitory cytokine-1 concentrations correlate with the presence of prostate cancer bone metastases.
Cancer Epidemiol Biomarkers Prev. 2007 March; 16(3): 532-7.
Golkar L, Ding X Z, Ujiki M B, Salabat M R, Kelly D L, Scholtens D, Fought A J, Bentrem D J, Talamonti M S, Bell R H, Adrian T E.
Resveratrol inhibits pancreatic cancer cell proliferation through transcriptional induction of macrophage inhibitory cytokine-1.
J Surg Res. 2007 April; 138(2): 163-9. Epub 2007 Jan. 25.
Agarwal M K, Hastak K, Jackson M W, Breit S N, Stark G R, Agarwal M L.
Macrophage inhibitory cytokine 1 mediates a p53-dependent protective arrest in S phase in response to starvation for DNA precursors.
Proc Natl Acad Sci USA. 2006 Oct. 31; 103(44): 16278-83. Epub 2006 Oct. 18.
Hayes V M, Severi G, Southey M C, Padilla E J, English D R, Hopper J L, Giles G G, Sutherland R L.
Macrophage inhibitory cytokine-1 H6D polymorphism, prostate cancer risk, and survival.

Cancer Epidemiol Biomarkers Prev. 2006 June; 15(6): 1223-5.
Martinez J M, Sali T, Okazaki R, Anna C, Hollingshead M, Hose C, Monks A, Walker N J, Baek S J, Eling T E.
Drug-induced expression of nonsteroidal anti-inflammatory drug-activated gene/macrophage inhibitory cytokine-1/prostate-derived factor, a putative tumor suppressor, inhibits tumor growth.
J Pharmacol Exp Ther. 2006 August; 318(2): 899-906. Epub 2006 May 19.
Bauskin A R, Brown D A, Kuffner T, Johnen H, Luo X W, Hunter M, Breit S N.
Role of macrophage inhibitory cytokine-1 in tumorigenesis and diagnosis of cancer.
Cancer Res. 2006 May 15; 66(10): 4983-6. Review.
Kadara H, Schroeder C P, Lotan D, Pisano C, Lotan R.
Induction of GDF-15/NAG-1/MIC-1 in human lung carcinoma cells by retinoid-related molecules and assessment of its role in apoptosis.
Cancer Biol Ther. 2006 May; 5(5): 518-22. Epub 2006 May 13.
Koopmann J, Rosenzweig C N, Zhang Z, Canto M I, Brown D A, Hunter M, Yeo C, Chan D W, Breit S N, Goggins M.
Serum markers in patients with resectable pancreatic adenocarcinoma: macrophage inhibitory cytokine 1 versus CA19-9.
Clin Cancer Res. 2006 Jan. 15; 12(2): 442-6.
Zimmers T A, Jin X, Hsiao E C, Perez E A, Pierce R H, Chavin K D, Koniaris L G.
Growth differentiation factor-15: induction in liver injury through p53 and tumor necrosis factor-independent mechanisms.
J Surg Res. 2006 January; 130(1): 45-51. Epub 2005 Sep. 12.
Shim M, Eling T E.
Protein kinase C-dependent regulation of NAG-1/placental bone morphogenic protein/MIC-1 expression in LNCaP prostate carcinoma cells.
J Biol Chem. 2005 May 13; 280(19): 18636-42. Epub 2005 Mar. 9.
Wollmann W, Goodman M L, Bhat-Nakshatri P, Kishimoto H, Goulet R J Jr, Mehrotra S, Morimiya A, Badve S, Nakshatri H.
The macrophage inhibitory cytokine integrates AKT/PKB and MAP kinase signaling pathways in breast cancer cells.
Carcinogenesis. 2005 May; 26(5): 900-7. Epub 2005 Jan. 27.
Lee S H, Kim J S, Yamaguchi K, Eling T E, Baek S J.
Indole-3-carbinol and 3,3'-diindolylmethane induce expression of NAG-1 in a p53-independent manner.
Biochem Biophys Res Commun. 2005 Mar. 4; 328(1): 63-9.
Cheung P K, Woolcock B, Adomat H, Sutcliffe M, Bainbridge T C, Jones E C, Webber D, Kinahan T, Sadar M, Gleave M E, Vielkind J.
Protein profiling of microdissected prostate tissue links growth differentiation factor 15 to prostate carcinogenesis.
Cancer Res. 2004 Sep. 1; 64(17): 5929-33.
Lindmark F, Zheng S L, Wiklund F, Bensen J, Balter K A, Chang B, Hedelin M, Clark J, Stattin P, Meyers D A, Adami H O, Isaacs W, Gronberg H, Xu J.
H6D polymorphism in macrophage-inhibitory cytokine-1 gene associated with prostate cancer.
J Natl Cancer Inst. 2004 Aug. 18; 96(16): 1248-54.
Koopmann J, Buckhaults P, Brown D A, Zahurak M L, Sato N, Fukushima N, Sokoll L J, Chan D W, Yeo C J, Hruban R H, Breit S N, Kinzler K W, Vogelstein B, Goggins M.
Serum macrophage inhibitory cytokine 1 as a marker of pancreatic and other periampullary cancers.
Clin Cancer Res. 2004 Apr. 1; 10(7): 2386-92.
Baek S J, Kim J S, Nixon J B, DiAugustine R P, Eling T E.
Expression of NAG-1, a transforming growth factor-beta superfamily member, by troglitazone requires the early growth response gene EGR-1.
J Biol Chem. 2004 Feb. 20; 279(8): 6883-92. Epub 2003 Dec. 8.
Tong S, Marjono B, Brown D A, Mulvey S, Breit S N, Manuelpillai U, Wallace E M.
Serum concentrations of macrophage inhibitory cytokine 1 (MIC 1) as a predictor of miscarriage.
Lancet. 2004 Jan. 10; 363(9403): 129-30.
Kim K S, Shin J H, Baek S J, Yoon J H.
Expression of non-steroidal anti-inflammatory drug-activated gene-1 in human nasal mucosa and cultured nasal epithelial cells: a preliminary investigation.
Acta Otolaryngol. 2003 September; 123(7): 857-61.
Keelan J A, Wang K, Chaiworapongsa T, Romero R, Mitchell M D, Sato T A, Brown D A, Fairlie W D, Breit S N.
Macrophage inhibitory cytokine 1 in fetal membranes and amniotic fluid from pregnancies with and without preterm labour and premature rupture of membranes.
Mol Hum Reprod. 2003 September; 9(9): 535-40.
Liu T, Bauskin A R, Zaunders J, Brown D A, Pankhurst S, Russell P J, Breit S N.
Macrophage inhibitory cytokine 1 reduces cell adhesion and induces apoptosis in prostate cancer cells.
Cancer Res. 2003 Aug. 15; 63(16): 5034-40. Erratum in: Cancer Res. 2004 Jan. 15; 64(2): 220. Panhurst, S [corrected to Pankhurst, S].
Brown D A, Ward R L, Buckhaults P, Liu T, Romans K E, Hawkins N J, Bauskin A R, Kinzler K W, Vogelstein B, Breit S N.
MIC-1 serum level and genotype: associations with progress and prognosis of colorectal carcinoma.
Clin Cancer Res. 2003 July; 9(7): 2642-50.
Iczkowski K A, Pantazis C G.
Overexpression of NSAID-activated gene product in prostate cancer.
Int J Surg Pathol. 2003 July; 11(3): 159-66.
Welsh J B, Sapinoso L M, Kern S G, Brown D A, Liu T, Bauskin A R, Ward R L, Hawkins N J, Quinn D I, Russell P J, Sutherland R L, Breit S N, Moskaluk C A, Frierson H F Jr, Hampton G M.
Large-scale delineation of secreted protein biomarkers overexpressed in cancer tissue and serum.
Proc Natl Acad Sci USA. 2003 Mar. 18; 100(6): 3410-5. Epub 2003 Mar. 6.
Subramaniam S, Strelau J, Unsicker K.

Growth differentiation factor-15 prevents low potassium-induced cell death of cerebellar granule neurons by differential regulation of Akt and ERK pathways.
J Biol Chem. 2003 Mar. 14; 278(11): 8904-12. Epub 2003 Jan. 3.
Strausberg R L, Feingold E A, Grouse L H, Derge J G, Klausner R D, Collins F S, Wagner L, Shenmen C M, Schuler G D, Altschul S F, Zeeberg B, Buetow K H, Schaefer C F, Bhat N K, Hopkins R F, Jordan H, Moore T, Max S I, Wang J, Hsieh F, Diatchenko L, Marusina K, Farmer A A, Rubin G M, Hong L, Stapleton M, Soares M B, Bonaldo M F, Casavant T L, Scheetz T E, Brownstein M J, Usdin T B, Toshiyuki S, Carninci P, Prange C, Raha S S, Loquellano N A, Peters G J, Abramson R D, Mullahy S J, Bosak S A, McEwan P J, McKernan K J, Malek J A, Gunaratne P H, Richards S, Worley K C, Hale S, Garcia A M, Gay L J, Hulyk S W, Villalon D K, Muzny D M, Sodergren E J, Lu X, Gibbs R A, Fahey J, Helton E, Ketteman M, Madan A, Rodrigues S, Sanchez A, Whiting M, Madan A, Young A C, Shevchenko Y, Bouffard G G, Blakesley R W, Touchman J W, Green E D, Dickson M C, Rodriguez A C, Grimwood J, Schmutz J, Myers R M, Butterfield Y S, Krzywinski M I, Skalska U, Smailus D E, Schnerch A, Schein J E, Jones S J, Marra M A; Mammalian Gene Collection Program Team.
Generation and initial analysis of more than 15,000 full-length human and mouse cDNA sequences.
Proc Natl Acad Sci USA. 2002 Dec. 24; 99(26): 16899-903. Epub 2002 Dec. 11.
Wong J, Li P X, Klamut H J.
A novel p53 transcriptional repressor element (p53TRE) and the asymmetrical contribution of two p53 binding sites modulate the response of the placental transforming growth factor-beta promoter to p53.
J Biol Chem. 2002 Jul. 19; 277(29): 26699-707. Epub 2002 May 14.
Graichen R, Liu D, Sun Y, Lee K O, Lobie P E.
Autocrine human growth hormone inhibits placental transforming growth factor-beta gene transcription to prevent apoptosis and allow cell cycle progression of human mammary carcinoma cells.
J Biol Chem. 2002 Jul. 19; 277(29): 26662-72. Epub 2002 May 6.
Brown D A, Bauskin A R, Fairlie W D, Smith M D, Liu T, Xu N, Breit S N.
Antibody-based approach to high-volume genotyping for MIC-1 polymorphism.
Biotechniques. 2002 July; 33(1): 118-20, 122, 124 passim.
Brown D A, Breit S N, Buring J, Fairlie W D, Bauskin A R, Liu T, Ridker P M.
Concentration in plasma of macrophage inhibitory cytokine-1 and risk of cardiovascular events in women: a nested case-control study.
Lancet. 2002 Jun. 22; 359(9324): 2159-63.
Albertoni M, Shaw P H, Nozaki M, Godard S, Tenan M, Hamou M F, Fairlie D W, Breit S N, Paralkar V M, de Tribolet N, Van Meir E G, Hegi M E.
Anoxia induces macrophage inhibitory cytokine-1 (MIC-1) in glioblastoma cells independently of p53 and HIF-1.
Oncogene. 2002 Jun. 20; 21(27): 4212-9.
Baek S J, Wilson L C, Eling T E.
Resveratrol enhances the expression of non-steroidal anti-inflammatory drug-activated gene (NAG-1) by increasing the expression of p53.
Carcinogenesis. 2002 March; 23(3): 425-34.
Buckhaults P, Rago C, St Croix B, Romans K E, Saha S, Zhang L, Vogelstein B, Kinzler K W.
Secreted and cell surface genes expressed in benign and malignant colorectal tumors.
Cancer Res. 2001 Oct. 1; 61(19): 6996-7001.
Baek S J, Horowitz J M, Eling T E.
Molecular cloning and characterization of human nonsteroidal anti-inflammatory drug-activated gene promoter. Basal transcription is mediated by Sp1 and Sp3.
J Biol Chem. 2001 Sep. 7; 276(36): 33384-92. Epub 2001 Jul. 9.
Fairlie W D, Zhang H P, Wu W M, Pankhurst S L, Bauskin A R, Russell P K, Brown P K, Breit S N.
The propeptide of the transforming growth factor-beta superfamily member, macrophage inhibitory cytokine-1 (MIC-1), is a multifunctional domain that can facilitate protein folding and secretion.
J Biol Chem. 2001 May 18; 276(20): 16911-8. Epub 2001 Feb. 26.
Baek S J, Kim K S, Nixon J B, Wilson L C, Eling T E.
Cyclooxygenase inhibitors regulate the expression of a TGF-beta superfamily member that has proapoptotic and antitumorigenic activities.
Mol Pharmacol. 2001 April; 59(4): 901-8.
Fairlie W D, Russell P K, Wu W M, Moore A G, Zhang H P, Brown P K, Bauskin A R, Breit S N.
Epitope mapping of the transforming growth factor-beta superfamily protein, macrophage inhibitory cytokine-1 (MIC-1): identification of at least five distinct epitope specificities.
Biochemistry. 2001 Jan. 9; 40(1): 65-73.
Moore A G, Brown D A, Fairlie W D, Bauskin A R, Brown P K, Munier M L, Russell P K, Salamonsen L A, Wallace E M, Breit S N.
The transforming growth factor-ss superfamily cytokine macrophage inhibitory cytokine-1 is present in high concentrations in the serum of pregnant women.
J Clin Endocrinol Metab. 2000 December; 85(12): 4781-8.
Strelau J, Sullivan A, Bottner M, Lingor P, Falkenstein E, Suter-Crazzolara C, Galter D, Jaszai J, Krieglstein K, Unsicker K.
Growth/differentiation factor-15/macrophage inhibitory cytokine-1 is a novel trophic factor for midbrain dopaminergic neurons in vivo,
J Neurosci. 2000 Dec. 1; 20(23): 8597-603.
Fairlie W D, Zhang H, Brown P K, Russell P K, Bauskin A R, Breit S N.
Expression of a TGF-beta superfamily protein, macrophage inhibitory cytokine-1, in the yeast *Pichia pastoris*.
Gene. 2000 Aug. 22; 254(1-2): 67-76.
Li P X, Wong J, Ayed A, Ngo D, Brade A M, Arrowsmith C, Austin R C, Klamut H J.
Placental transforming growth factor-beta is a downstream mediator of the growth arrest and apoptotic response of tumor cells to DNA damage and p53 overexpression.
J Biol Chem. 2000 Jun. 30; 275(26): 20127-35.
Bauskin A R, Zhang H P, Fairlie W D, He X Y, Russell P K, Moore A G, Brown D A, Stanley K K, Breit S N.
The propeptide of macrophage inhibitory cytokine (MIC-1), a TGF-beta superfamily member, acts as a quality control determinant for correctly folded MIC-1.

-continued

EMBO J. 2000 May 15; 19(10): 2212-20.
Fairlie W D, Moore A G, Bauskin A R, Russell P K, Zhang H P, Breit S N.
MIC-1 is a novel TGF-beta superfamily cytokine associated with macrophage activation.
J Leukoc Biol. 1999 January; 65(1): 2-5. Review.
Bottner M, Laaff M, Schechinger B, Rappold G, Unsicker K, Suter-Crazzolara C.
Characterization of the rat, mouse, and human genes of growth/differentiation factor-15/macrophage inhibiting cytokine-1 (GDF-15/MIC-1).
Gene. 1999 Sep. 3; 237(1): 105-11.
Paralkar V M, Vail A L, Grasser W A, Brown T A, Xu H, Vukicevic S, Ke H Z, Qi H, Owen T A, Thompson D D.
Cloning and characterization of a novel member of the transforming growth factor-beta/bone morphogenetic protein family.
J Biol Chem. 1998 May 29; 273(22): 13760-7.
Lawton L N, Bonaldo M F, Jelenc P C, Qiu L, Baumes S A, Marcelino R A, de Jesus G M, Wellington S, Knowles J A, Warburton D, Brown S, Soares M B.
Identification of a novel member of the TGF-beta superfamily highly expressed in human placenta.
Gene. 1997 Dec. 5; 203(1): 17-26.
Bootcov M R, Bauskin A R, Valenzuela S M, Moore A G, Bansal M, He X Y, Zhang H P, Donnellan M, Mahler S, Pryor K, Walsh B J, Nicholson R C, Fairlie W D, Por S B, Robbins J M, Breit S N.
MIC-1, a novel macrophage inhibitory cytokine, is a divergent member of the TGF-beta superfamily.
Proc Natl Acad Sci USA. 1997 Oct. 14; 94(21): 11514-9.
Hromas R, Hufford M, Sutton J, Xu D, Li Y, Lu L.
PLAB, a novel placental bone morphogenetic protein.
Biochim Biophys Acta. 1997 Oct. 9; 1354(1): 40-4.
Yokoyama-Kobayashi M, Saeki M, Sekine S, Kato S.
Human cDNA encoding a novel TGF-beta superfamily protein highly expressed in placenta.
J Biochem (Tokyo). 1997 September; 122(3): 622-6.

As described in the publications above, MIC-1/GDF-15 (PCan065) is secreted as a dimer with an approximate relative molecular mass of 24-30 kDa. The 308 amino acid protein is characterized by N-terminal signal peptide sequence from amino acids 1-29; an N-glycosylation site at amino acid 70; a proteolytic cleavage site at amino acid 196; a disulfide bridge bond at amino acid 203, 211 or 273; and a transforming growth factor-beta (TGF-beta) domain from amino acids 207-308, 208-308 or 211-308. MIC-1 is expressed by cells as disulfide linked dimmer (Bausin et al. 2000, supra). It has been shown that PCan065/MIC-1 is differentially expressed in prostate, pancreatic and colon cancer versus normal tissues. MIC-1 has cytokine activity to control the survival, growth, differentiation and effector function of tissues and cells; and growth factor activity that stimulates a cell to grow or proliferate. Additionally, MIC-1 plays a role in the regulation of a number of processes including apoptosis, cell and growth differentiation, MAP kinase signaling, signal transduction, cell adhesion, low potassium-induced cell death of cerebellar granule neurons, p53 associated expression, tumorigenesis and events such as miscarriage, pregnancy, and cardiovascular events. Specifically, TGF-beta is a multifunctional peptide that controls proliferation, differentiation, and other functions in many cell types.

Also described and known in the literature are antibodies against MIC-1/GDF-15 such as sheep anti-MICA polyclonal antibody 233B3 and mouse anti-MIC-1 monoclonal antibody 13C4H3 (Moore et al. 2000, supra); mouse anti-MICA monoclonal antibody producing hybridomas 13, 26, 10, 14 (Fairlie W D et al. 2001, supra); mouse anti-MIC-1 monoclonal antibody 26G6H6 (Brown et al., Biotechniques 2002, supra); goat anti-MIC-1/GDF-15 polyclonal antibody, catalogue No. AF957, from R&D Systems (Minneapolis, Minn.); and rabbit anti-MIC-1/GDF-15 polyclonal antibody, catalogue No. PAB-10692, from Orbigen (San Diego, Calif.). The disclosure, characterization and use of these antibodies and antibody producing hybridomas in their respective publications are herein incorporated by reference.

The antibodies of the instant invention specifically bind PCan065 and have demonstrated characteristics which make them ideal therapeutic candiates for modulating PCan065 activity or protein functions including TGF-beta domain activity, cytokine activity, and growth factor activity. Modulation of these functions is achieved by binding of an antibody to the functional domain and antagonisticly preventing the activity of the functional domain. Inhibition of PCan065 protein function may be also acheived by preventing or inhibiting activation of the PCan065 pro-protein into the functional mature protien. Since conversion of the pro-protein to the mature protein is dependant on cleave of the proteolytic cleavage site, an anti-PCan065 antibody which binds to the cleavage site, or creates a steric block of the site preventing cleavage, would inhibit PCan065 maturation and reduce PCan065 protein function. Alternatively, inhibition of PCan065 protein function may be acheived by disrupting, dissolving or preventing dimerization of PCan065 with an anti-PCan065 antibody.

Inhibition of PCan065 protein function results in inhibition or reduction of PCan065 biological functions. Anti-PCan065 antibodies which bind PCan065 inhibit or reduce PCan065 biological functions such as apoptosis, cell and growth differentiation, MAP kinase signaling, signal transduction, cell adhesion, low potassium-induced cell death of cerebellar granule neurons, p53 associated expression, tumorgenesis.

Furthermore, the antibodies of the instant invention are useful as therapeutic agents for individuals suffering from ovarian, breast, colon, prostate, pancreatic or lung cacrinomas. The antibodies may have therapeutic effect by killing PCan065 expressing cancer cells, inhibiting growth of PCan065 expressing tumors, shrinking PCan065 expressing tumors, extending survival time of individuals with PCan065 expressing tumors, reducing metastases of PCan065 expressing tumors, inducing immune response against PCan065 expressing tumors, reducing inhibition of immune response against PCan065 expressing tumors or reducing angiogenesis or vascularization of PCan065 expressing tumors.

Taken together, the differential expression in cancer and role in regulation of cellular processes, make PCan065 a promising target for diagnosis and immunotherapy of various tumor types. Anti-PCan065 antibodies are useful in diagnostic or therapeutic applications alone or in combination with antibodies against other GDF family members.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for [L and F isotypes. Each 6 L chain has at the N-terminus, a variable domain (VL) followed by a constant domain (CL) at its other end.

The VL is aligned with the VH and the CL is aligned with the first constant domain of the heavy chain (CHI).

Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993). Furthermore, effects of linker sequence alterations in engineering bispecific tandem diabodies are described in Le Gall et al., Protein Eng Des Sel. 17(4):357-66 (2004).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of PCan065 will possess at least about 70% homology with the native sequence PCan065, preferably, at least about 80%, more preferably at least about 85%, even more preferably at least about 90% homology, and most preferably at least 95%. The amino acid sequence variants can possess substitutions, deletions, insertions and/or alterations due to allelic variation or Single Nucleotide Polymorphisms (SNPs) within the native nucleic acid sequence encoding the amino acid sequence.

Several definitions of SNPs exist. See, e.g., Brooks, 235 Gene 177-86 (1999). As used herein, the term "single nucleotide polymorphism" or "SNP" includes all single base variants, thus including nucleotide insertions and deletions in addition to single nucleotide substitutions and any resulting amino acid variants due to codon alteration. There are two types of nucleotide substitutions. A transition is the replacement of one purine by another purine or one pyrimidine by another pyrimidine. A transversion is the replacement of a purine for a pyrimidine, or vice versa.

Numerous methods exist for detecting SNPs within a nucleotide sequence. A review of many of these methods can be found in Landegren et al., 8 Genome Res. 769-76 (1998). For example, a SNP in a genomic sample can be detected by preparing a Reduced Complexity Genome (RCG) from the genomic sample, then analyzing the RCG for the presence or absence of a SNP. See, e.g., WO 00/18960. Multiple SNPs in a population of target polynucleotides in parallel can be detected using, for example, the methods of WO 00/50869. Other SNP detection methods include the methods of U.S. Pat. Nos. 6,297,018 and 6,322,980. Furthermore, SNPs can be detected by restriction fragment length polymorphism (RFLP) analysis. See, e.g., U.S. Pat. Nos. 5,324,631; 5,645, 995. RFLP analysis of SNPs, however, is limited to cases where the SNP either creates or destroys a restriction enzyme cleavage site. SNPs can also be detected by direct sequencing of the nucleotide sequence of interest. In addition, numerous assays based on hybridization have also been developed to detect SNPs and mismatch distinction by polymerases and ligases. Several web sites provide information about SNPs including Ensembl (ensembl with the extension .org of the world wide web), Sanger Institute (sanger with the extension .ac.uk/genetics/exon/ of the world wide web), National Center for Biotechnology Information (NCBI) (ncbi with the extension .nlm.nih.gov/SNP/ of the world wide web), The SNP Consortium Ltd. (snp with the extension .cshl.org of the world wide web). The chromosomal locations for the compositions disclosed herein are provided below. In addition, one of ordinary skill in the art could perform a search against the genome or any of the databases cited above using BLAST to find the chromosomal location or locations of SNPs. Another a preferred method to find the genomic coordinates and associated SNPs would be to use the BLAT tool (genome.ucsc.edu, Kent et al. 2001, The Human Genome Browser at UCSC, Genome Research 996-1006 or Kent 2002 BLAT, The BLAST-Like Alignment Tool Genome Research, 1-9). All web sites above were accessed Dec. 3, 2003.

Preferred amino acid sequence variants of PCan065 are described in the table below. The nucleic acid and amino acid sequences of PCan065 are disclosed in the references cited above, which are incorporated by reference in their entirety. The polynucleotides encoding the amino acids of the present invention were analyzed and single nucleotide polymorphism (SNP) attributes were identified. Specifically identified were SNPs occurring the coding region of the nucleotide, the Alleles of the SNP, the nucleotide ambiguity code for the SNP, the position in the codon of the SNP if within the Open Reading Frame (1, 2, 3 or UTR for untranslated regions), and the SNP type (synonymous or non-synonymous to the protein translation). In addition to the attributes above, the SNP rs# ID for the NCBI SNP database (dbSNP) which is accessible at ncbi with the extension .nlm.nih.gov/SNP/ of the world wide web is referenced for each SNP. Additional single nucleotide polymorphism (SNP) information can be accessed at the databases listed above.

The table below includes the polynucleotide target, dbSNP rs# ID, Nucleic acid residue affected by the SNP (Polynucleotide) in NM_004864, SNP alleles, Nucleotide ambiguity code, Condon Position of the SNP if within the ORF (1, 2, 3 or UTR if not within ORF), and the SNP type (synonymous "syn" or non-synonymous "non-syn"), Amino acid residue affected by the SNP (AA Residue) in NP_003814, and the Alternate amino acid residue.

Variants of PCan065 as described above and antibodies which bind to these variants individually or in combination are part of the invention described herein. Antibodies of instant invention may have diagnostic or thereapeutic utility for the variants of PCan065 outlined above.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, CUM Op. Struct. Biol. 2:593-596 (1992).

| dbSNP rs# ID | Nucleic Acid Residue | Alleles | Ambiguity Code | Codon Pos | SNP type | Amino Acid Residue | Alternate Amino Acid |
|---|---|---|---|---|---|---|---|
| 1059519 | 50 | C/G | S | 1 | Non-syn | 9 | L/V |
| 17526133 | 50 | C/G | S | 1 | Non-syn | 9 | L/V |
| 6413435 | 163 | A/G | R | 3 | Syn | 46 | L/L |
| 1059369 | 167 | A/T | W | 1 | Non-syn | 48 | T/S |
| 17526140 | 167 | A/T | W | 1 | Non-syn | 48 | T/S |
| 17655466 | 167 | A/T | W | 1 | Non-syn | 48 | T/S |
| 16982331 | 188 | G/T | K | 1 | Non-syn | 55 | E/[stop] |
| 1059022 | 358 | T/C | R | 3 | Syn | 111 | P/P |
| 1804826 | 455 | T/G | K | 3 | Syn | 140 | P/P |
| 3746195 | 497 | A/C | M | 1 | Syn | 158 | R/R |
| 1058587 | 629 | G/C | S | 1 | Non-syn | 202 | D/H |
| 1064601 | 770 | G/C | S | 1 | Non-syn | 249 | G/R |
| 11556750 | 840 | A/C | M | 2 | Non-syn | 272 | H/P |

As used herein, an anti-PCan065 antibody that "internalizes" is one that is taken up by (i.e., enters) the cell upon binding to PCan065 on a mammalian cell (i.e. cell surface PCan065). The internalizing antibody will of course include antibody fragments, human or humanized antibody and antibody conjugate. For therapeutic applications, internalization in vivo is contemplated. The number of antibody molecules internalized will be sufficient or adequate to kill an PCan065-expressing cell, especially an PCan065-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-PCan065 antibody internalizes upon binding PCan065 on a mammalian cell can be determined by various assays including those described in the experimental examples below. For example, to test internalization in vivo, the test antibody is labeled and introduced into an animal known to have PCan065 expressed on the surface of certain cells. The antibody can be radiolabeled or labeled with fluorescent or gold particles, for instance. Animals suitable for this assay include a mammal such as a NCR nude mouse that contains a human PCan065-expressing tumor transplant or xenograft, or a mouse into which cells transfected with human PCan065 have been introduced, or a transgenic mouse expressing the human PCan065 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising PCan065-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the PCan065-expressing cell in vivo, the faster the desired killing or growth inhibitory effect on the target PCan065-expressing cell can be achieved, e.g., by a cytotoxic immunoconjugate. Preferably, the kinetics of internalization of the anti-PCan065 antibodies are such that they favor rapid killing of the PCan065-expressing target cell. Therefore, it is desirable that the anti-PCan065 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-PCan065 antibody in vivo. The antibody will preferably be internalized into the cell within a few hours upon binding to PCan065 on the cell surface, preferably within 1 hour, even more preferably within 15-30 minutes. To determine if a test antibody can compete for binding to the same epitope as the epitope bound by the anti-PCan065 antibodies of the present invention including the antibodies produced by the hybridomas deposited with the ATCC, a cross-blocking assay e.g., a competitive ELISA assay can be performed. In an exemplary competitive ELISA assay, PCan065-coated wells of a microtiter plate, or PCan065-coated SEPHAROSE® (high molecular weight substance for the separation by gel filtration of macromolecules (such as viruses, proteins and blood serums) that range in weight from about 100,000 to several million (GE Healthcare Bio-Sciences Ab Ltd Liab Co Uppsala, Sweden) beads, are pre-incubated with or without candidate competing antibody and then a biotin-labeled anti-PCan065 antibody of the invention is added. The amount of labeled anti-PCan065 antibody bound to the PCan065 antigen in the wells or on the beads is measured using avidin-peroxidase conjugate and appropriate substrate.

Alternatively, the anti-PCan065 antibody can be labeled, e.g., with a radioactive or fluorescent label or some other detectable and measurable label. The amount of labeled anti-PCan065 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-PCan065 antibody will be bound to the antigen-coated wells. A candidate competing antibody is considered an antibody that binds substantially to the same epitope or that competes for binding to the same epitope as an anti-PCan065 antibody of the invention if the candidate competing antibody can block binding of the anti-PCan065 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies PCan065.A4, PCan065.A10, PCan065.A13, PCan065.B1, PCan065.B2, PCan065.B3, PCan065.B4, PCan065.B5, PCan065.B6, PCan065.B7, PCan065.B8, PCan065.B9, PCan065.B10, PCan065.B11, PCan065.B12, PCan065.B13, PCan065.B14, PCan065.B15, PCan065.B16, PCan065.B17, PCan065.B18, PCan065.B19, PCan065.B20, PCan065.B21, PCan065.B22, PCan065.B23, PCan065.B24, PCan065.B25, PCan065.B26, PCan065.B27, PCan065.B28, PCan065.B29, PCan065.B30, PCan065.B31, PCan065.B32, PCan065.B33, PCan065.B34, PCan065.B35, PCan065.B36, PCan065.B37, PCan065.B38, PCan065.B39, PCan065.B40, PCan065.B41, PCan065.B42, PCan065.B43, PCan065.B44, PCan065.B45, PCan065.B46, PCan065.B47, PCan065.B48, PCan065.B101, PCan065.B102, PCan065.B103, PCan065.B104, PCan065.B105, PCan065.B106, PCan065.B107, PCan065.B108, PCan065.B109, PCan065.B110, PCan065.B111, PCan065.B112, PCan065.B113, PCan065.B114, PCan065.B115, PCan065.B116, PCan065.B117 and PCan065.B118, is one which possesses one or more of the biological characteristics of that antibody which distinguish it from other antibodies that bind to the same antigen, PCan065.A4, PCan065.A10, PCan065.A13, PCan065.B1, PCan065.B2, PCan065.B3, PCan065.B4, PCan065.B5, PCan065.B6, PCan065.B7, PCan065.B8, PCan065.B9, PCan065.B10, PCan065.B11, PCan065.B12, PCan065.B13, PCan065.B14, PCan065.B15, PCan065.B16, PCan065.B17, PCan065.B18, PCan065.B19, PCan065.B20, PCan065.B21, PCan065.B22, PCan065.B23, PCan065.B24, PCan065.B25, PCan065.B26, PCan065.B27, PCan065.B28, PCan065.B29, PCan065.B30, PCan065.B31, PCan065.B32, PCan065.B33, PCan065.B34, PCan065.B35, PCan065.B36, PCan065.B37, PCan065.B38, PCan065.B39, PCan065.B40, PCan065.B41, PCan065.B42, PCan065.B43, PCan065.B44, PCan065.B45, PCan065.B46, PCan065.B47, PCan065.B48, PCan065.B101, PCan065.B102, PCan065.B103, PCan065.B104, PCan065.B105, PCan065.B106, PCan065.B107, PCan065.B108, PCan065.B109, PCan065.B110, PCan065.B111, PCan065.B112, PCan065.B113, PCan065.B114, PCan065.B115, PCan065.B116, PCan065.B117 and PCan065.B118, will bind the same epitope as that bound by PCan065.A4, PCan065.A10, PCan065.A13, PCan065.B1, PCan065.B2, PCan065.B3, PCan065.B4, PCan065.B5, PCan065.B6, PCan065.B7, PCan065.B8, PCan065.B9, PCan065.B10, PCan065.B11, PCan065.B12, PCan065.B13, PCan065.B14, PCan065.B15, PCan065.B16, PCan065.B17, PCan065.B18, PCan065.B19, PCan065.B20, PCan065.B21, PCan065.B22, PCan065.B23, PCan065.B24, PCan065.B25, PCan065.B26, PCan065.B27, PCan065.B28, PCan065.B29, PCan065.B30, PCan065.B31, PCan065.B32, PCan065.B33, PCan065.B34, PCan065.B35, PCan065.B36, PCan065.B37, PCan065.B38, PCan065.B39, PCan065.B40, PCan065.B41, PCan065.B42, PCan065.B43, PCan065.B44, PCan065.B45, PCan065.B46, PCan065.B47, PCan065.B48, PCan065.B101, PCan065.B102, PCan065.B103, PCan065.B104, PCan065.B105, PCan065.B106, PCan065.B107, PCan065.B108, PCan065.B109, PCan065.B110, PCan065.B111, PCan065.B112, PCan065.B113, PCan065.B114, PCan065.B115, PCan065.B116, PCan065.B117 and PCan065.B118, (e.g. which competes for binding or blocks binding of monoclonal antibody PCan065.A4, PCan065.A10, PCan065.A13, PCan065.B1, PCan065.B2, PCan065.B3, PCan065.B4, PCan065.B5, PCan065.B6, PCan065.B7, PCan065.B8, PCan065.B9, PCan065.B10, PCan065.B11, PCan065.B12, PCan065.B13, PCan065.B14, PCan065.B15, PCan065.B16, PCan065.B17, PCan065.B18, PCan065.B19, PCan065.B20, PCan065.B21, PCan065.B22, PCan065.B23, PCan065.B24, PCan065.B25, PCan065.B26, PCan065.B27, PCan065.B28, PCan065.B29, PCan065.B30, PCan065.B31, PCan065.B32, PCan065.B33, PCan065.B34, PCan065.B35, PCan065.B36, PCan065.B37, PCan065.B38, PCan065.B39, PCan065.B40, PCan065.B41, PCan065.B42, PCan065.B43, PCan065.B44, PCan065.B45, PCan065.B46, PCan065.B47, PCan065.B48, PCan065.B101, PCan065.B102, PCan065.B103, PCan065.B104, PCan065.B105, PCan065.B106, PCan065.B107, PCan065.B108, PCan065.B109, PCan065.B110, PCan065.B111, PCan065.B112, PCan065.B113, PCan065.B114, PCan065.B115, PCan065.B116, PCan065.B117 and PCan065.B118,), be able to target an PCan065-expressing tumor in vivo and may internalize upon binding to PCan065 on a mammalian cell in vivo. Likewise, an antibody with the biological characteristic of the PCan065.A4, PCan065.A10, PCan065.A13, PCan065.B1, PCan065.B2, PCan065.B3, PCan065.B4, PCan065.B5, PCan065.B6, PCan065.B7, PCan065.B8, PCan065.B9, PCan065.B10, PCan065.B11, PCan065.B12, PCan065.B13, PCan065.B14, PCan065.B15, PCan065.B16, PCan065.B17, PCan065.B18, PCan065.B19, PCan065.B20, PCan065.B21, PCan065.B22, PCan065.B23, PCan065.B24, PCan065.B25, PCan065.B26, PCan065.B27, PCan065.B28, PCan065.B29, PCan065.B30, PCan065.B31, PCan065.B32, PCan065.B33, PCan065.B34, PCan065.B35, PCan065.B36, PCan065.B37, PCan065.B38, PCan065.B39, PCan065.B40, PCan065.B41, PCan065.B42, PCan065.B43, PCan065.B44, PCan065.B45, PCan065.B46, PCan065.B47, PCan065.B48, PCan065.B101, PCan065.B102, PCan065.B103, PCan065.B104, PCan065.B105, PCan065.B106, PCan065.B107, PCan065.B108, PCan065.B109, PCan065.B110, PCan065.B111, PCan065.B112, PCan065.B113, PCan065.B114, PCan065.B115, PCan065.B116, PCan065.B117 and PCan065.B118 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native PCan065 protein disclosed herein. Methods for identifying antagonists of an PCan065 polypeptide may comprise contacting an PCan065 polypeptide or a cell expressing PCan065 on the cell surface, with a candidate antagonist antibody and measuring a detectable change in one or more biological activities normally associated with the PCan065 polypeptide.

The term 'agonistic' antibody is used in the broadest sense, and includes an antibody the partially or fully promotes, activates, or increases biological activity of PCan065. Additionally, an agonistic antibody may mimic an PCan065 binding partner (e.g. receptor or ligand) wherein binding of the PCan065 antibody has substantially the same effect on biologic activity of PCan065 as binding of the binding partner. Methods for identifying agonists of an PCan065 polypeptide may comprise contacting an PCan065 polypeptide or a cell expressing PCan065 on the cell surface, with a candidate agonistic antibody and measuring a detectable change in one or more biological activities normally associated with the PCan065 polypeptide.

An "antibody that inhibits the growth of tumor cells expressing PCan065" or a "growth inhibitory" antibody is one which binds to and results in measurable growth inhibition of cancer cells expressing or overexpressing PCan065. Preferred growth inhibitory anti-PCan065 antibodies inhibit growth of PCan065-expressing tumor cells (e.g., ovarian, colon, prostate or lung cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-PCan065 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses PCan065. Preferably the cell is a tumor cell, e.g. an ovarian, colon, prostate, or lung cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); complement dependent cytotoxicity (CDC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRI1B contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "PCan065-expressing cell" is a cell which expresses endogenous or transfected PCan065 on the cell surface or secretes endogenous or transfected PCan065. A "PCan065-expressing cancer" is a cancer comprising cells that have PCan065 protein present on the cell surface or secretes PCan065 from the cell. A "PCan065-expressing cancer" produces sufficient levels of PCan065 on the surface of cells thereof or secretes PCan065 from the cells thereof, such that an anti-PCan065 antibody can bind thereto and have a therapeutic effect with respect to the cancer. A cancer which "overexpresses" PCan065 is one which has significantly higher levels of PCan065 at the cell surface thereof or secretes PCan065 from the cells thereof, compared to a noncancerous cell of the same tissue type. Such overexpression may be caused by gene amplification or by increased transcription or translation. PCan065 overexpression may be determined in a diagnostic or prognostic assay by evaluating increased levels of the PCan065 protein present on the surface of a cell (e.g. via an immunohistochemistry assay; FACS analysis). Alternatively, or additionally, one may measure levels of PCan065-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study PCan065 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401, 638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. An PCan065-expressing cancer includes ovarian, breast, colon, prostate, pancreatic or lung cancer.

A "mammal" for purposes of treating a cancer or alleviating the symptoms of cancer, refers to any mammal, including-humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an PCan065-expressing cancer if, after receiving a therapeutic amount of an anti-PCan065 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-PCan065 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially an PCan065-expressing cancer cell, either in vitro or in vivo. Thus, the growth inhibitory agent may be one which significantly reduces the percentage of PCan065-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-PCan065 antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColEl origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-PCan065 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in *C. Elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxynucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-0 or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a *Drosophila* in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsRNAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of *C. elegans*. Tuschl et al., International PCT Publication No. WO 02/44321, describe certain synthetic siRNA constructs.

Compositions and Methods of the Invention

The invention provides anti-PCan065 antibodies. Preferably, the anti-PCan065 antibodies internalize upon binding to cell surface PCan065 on a mammalian cell. The anti-PCan065 antibodies may also destroy or lead to the destruction of tumor cells expressing PCan065.

It was not apparent that PCan065 was internalization-competent. In addition the ability of an antibody to internalize depends on several factors including the affinity, avidity, and isotype of the antibody, and the epitope that it binds. We have demonstrated herein that the cell surface PCan065 is internalization competent upon binding by the anti-PCan065 antibodies of the invention. Additionally, it was demonstrated that the anti-PCan065 antibodies of the present invention can specifically target PCan065-expressing tumor cells. These tumor targeting, internalization and growth inhibitory properties of the anti-PCan065 antibodies make these antibodies very suitable for therapeutic uses, e.g., in the treatment of various cancers including ovarian, breast, colon, prostate, pancreatic or lung cancer. Internalization of the anti-PCan065 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-PCan065 antibodies of the invention also have various non-therapeutic applications. The anti-PCan065 antibodies of the present invention can be useful for diagnosis and staging of PCan065-expressing cancers (e.g., in radioimaging). They may be used alone or in combination with other ovarian cancer markers, including, but not limited to, CA125, HE4 and mesothelin. The antibodies are also useful for purification or immunoprecipitation of PCan065 from cells, for detection and quantitation of PCan065 in vitro, e.g. in an ELISA or a Western blot, to kill and eliminate PCan065-expressing cells from a population of mixed cells as a step in the purification of other cells. The internalizing anti-PCan065 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-PCan065 antibodies of the invention are also contemplated, e.g., an anti-PCan065 antibody which has the biological characteristics of a monoclonal antibody produced by the hybridomas deposited with the ATCC comprising PCan065.A10.3.2 and PCan065.B2.2.1, specifically including the in vivo tumor targeting, internalization and any cell proliferation inhibition or cytotoxic characteristics. Specifically provided are anti-PCan065 antibodies that bind to an epitope present in amino acids 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 301-308 or 1-15, 10-25, 15-25, 21-35, 31-45, 41-55, 51-65, 61-75, 71-85, 81-95, 91-105, 101-115, 111-125, 121-135, 131-145, 141-155, 151-165, 161-175, 171-185, 181-195, 191-205, 201-215, 211-225, 221-235, 231-245, 241-255, 251-265, 261-275, 271-285, 281-295, 291-300, 295-308 of human PCan065.

Methods of producing the above antibodies are described in detail below.

The present anti-PCan065 antibodies are useful for treating a PCan065-expressing cancer or alleviating one or more symptoms of the cancer in a mammal. Such a cancer includes ovarian, breast, colon, prostate, pancreatic or lung cancer, cancer of the urinary tract, lung cancer, breast cancer, colon cancer, pancreatic cancer, and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding, e.g., ovarian, breast, colon, prostate, pancreatic or lung cancer metastases. The antibody is able to bind to at least a portion of the cancer cells that express PCan065 in the mammal and preferably is one that does not induce or that minimizes HAMA response. Preferably, the antibody is effective to destroy or kill PCan065-expressing tumor cells or inhibit the growth of such tumor cells, in vitro or in vivo, upon binding to PCan065 on the cell. Such an antibody includes a naked anti-PCan065 antibody (not conjugated to any agent). Naked anti-PCan065 antibodies having tumor growth inhibition properties in vivo include the antibodies described in the Experimental Examples below. Naked antibodies that have cytotoxic or cell growth inhibition properties can be further conjugated with a cytotoxic agent to render them even more potent in tumor cell destruction. Cytotoxic properties can be conferred to an anti-PCan065 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-PCan065 antibody of the invention, and a carrier. For the purposes of treating cancer, compositions can be administered to the patient in need of such treatment, wherein the composition can comprise one or more anti-PCan065 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-PCan065 antibody of the invention, and a carrier. The formulation may be a therapeutic formulation comprising a pharmaceutically acceptable carrier.

Another aspect of the invention is isolated nucleic acids encoding the internalizing anti-PCan065 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating an PCan065-expressing cancer or alleviating one or more symptoms of the cancer in a mammal, comprising administering a therapeutically effective amount of an internalizing anti-PCan065 antibody to the mammal. The antibody therapeutic compositions can be administered short term (acute) or chronic, or intermittent as directed by physician. Also provided are methods of inhibiting the growth of, and killing an PCan065 expressing cell. Finally, the invention also provides kits and articles of manufacture comprising at least one antibody of this invention, preferably at least one internalizing anti-PCan065 antibody of this invention. Kits containing anti-PCan065 antibodies find use in detecting PCan065 expression, or in therapeutic or diagnostic assays, e.g., for PCan065 cell killing assays or for purification and/or immunoprecipitation of PCan065 from cells, tissues or bodily fluids. For example, for isolation and purification of PCan065, the kit can contain an anti-PCan065 antibody coupled to a solid support, e.g., a tissue culture plate or beads (e.g., SEPHAROSE® beads). Kits can be provided which contain antibodies for detection and quantitation of PCan065 in vitro, e.g. in an ELISA or a Western blot. Such antibody useful for detection may be provided with a label such as a fluorescent or radiolabel.

Production of Anti-PCan065 Antibodies

The following describes exemplary techniques for the production of the antibodies useful in the present invention. Some of these techniques are described further in Example 1. The PCan065 antigen to be used for production of antibodies may be, e.g., the full length polypeptide or a portion thereof, including a soluble form of PCan065 lacking the membrane spanning sequence, or synthetic peptides to selected portions of the protein.

Alternatively, cells expressing PCan065 at their cell surface (e.g. CHO or NIH-3T3 cells transformed to overexpress PCan065; ovarian, pancreatic, lung, breast or other PCan065-expressing tumor cell line), or membranes prepared from such cells can be used to generate antibodies. The nucleotide and amino acid sequences of human and murine PCan065 are available as provided above. PCan065 can be produced recombinantly in and isolated from, prokaryotic cells, e.g., bacterial cells, or eukaryotic cells using standard recombinant DNA methodology. PCan065 can be expressed as a tagged (e.g., epitope tag) or other fusion protein to facilitate its isolation as well as its identification in various assays.

Antibodies or binding proteins that bind to various tags and fusion sequences are available as elaborated below. Other forms of PCan065 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g., the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-II mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-SEPHAROSE®) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., *E coli* cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PCan065 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the PCan065 protein. Other such antibodies may combine an PCan065 binding site with a binding site for another protein. Alternatively, an anti-PCan065.Arm may be combined with an arm which binds to a triggering molecule on a leukocyte such as a Tcell receptor molecule (e.g. C133), or Fc receptors for IgG (FcγR), such as FcγRI (CD64), FcγRII (CD32) and FcγRIII (CD16), so as to focus and localize cellular defense mechanisms to the PCan065-expressing cell. Bispecific antibodies may also be used to localize cytotoxic agents to cells which express PCan065. These antibodies possess an PCan065-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VDI is a first variable domain, VD2 is a second variable domain, Fc is one polypeptide chain of an Fc region, XI and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-PCan065 antibodies described herein are contemplated. For example, it may be desirable to improve the binding affinity and/or other biological properties of the antibody. Amino acid sequence variants of the anti-PCan065 antibody are prepared by introducing appropriate nucleotide changes into the anti-PCan065 antibody nucleic acid, or by peptide synthesis.

Such modifications include, for example, deletions from, and/or insertions into, and/or substitutions of, residues within the amino acid sequences of the anti-PCan065 antibody. Any combination of deletion, insertion, and substitution is made to arrive at the final construct, provided that the final construct possesses the desired characteristics. The amino acid changes also may alter post-translational processes of the anti-PCan065 antibody, such as changing the number or position of glycosylation sites.

A useful method for identification of certain residues or regions of the anti-PCan065 antibody that are preferred locations for mutagenesis is called "alanine scanning mutagenesis" as described by Cunningham and Wells in Science, 244:1081-1085 (1989). Here, a residue or group of target residues within the anti-PCan065 antibody are identified (e.g., charged residues such as arg, asp, his, lys, and glu) and replaced by a neutral or negatively charged amino acid (most preferably alanine or polyalanine) to affect the interaction of the amino acids with PCan065 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-PCan065 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-PCan065 antibody with an N-terminal methionyl residue or the antibody fused to a cytotoxic polypeptide. Other insertional variants of the anti-PCan065 antibody molecule include the fusion to the N- or C-terminus of the anti-PCan065 antibody to an enzyme (e.g. for ADEPT) or a fusion to a polypeptide which increases the serum half-life of the antibody.

Another type of variant is an amino acid substitution variant. These variants have at least one amino acid residue in the anti-PCan065 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in the table below, or as further described below in reference to amino acid classes, may be introduced and the products screened for a desired characteristic.

Amino Acid Substitutions

| Original Residue | Exemplary Substitutions | Preferred Substitutions |
|---|---|---|
| Ala (A) | val; leu; ile | Val |
| Arg (R) | lys; g1n; asn | lys |
| Asn (N) | g1n; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; g1n; lys; arg | arg |
| Ile (I) | leu; val; met; ala; phe; norleucine | leu |
| Leu (L) | norleucine; ile; val; met; ala; phe | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr(Y) | trp; phe; thr; ser | Phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-PCan065 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human PCan065. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-PCan065 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-PCan065 antibody.

It may be desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced antitumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The growth inhibitory effects of an anti-PCan065 antibody of the invention may be assessed by methods known in the art, e.g., using cells which express PCan065 either endogenously or following transfection with the PCan065 gene. For example, the tumor cell lines and PCan065-transfected cells provided in Example 1 below may be treated with an anti-PCan065 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-PCan065 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses PCan065. Preferably, the anti-PCan065 antibody will inhibit cell proliferation of an PCan065-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-PCan065 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. PCan065-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on PCan065 bound by an antibody of interest, e.g., the PCan065 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-PCan065 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of PCan065 can be used in competition assays with the test antibodies or with a test antibody and an antibody with a characterized or known epitope.

For example, a method to screen for antibodies that bind to an epitope which is bound by an antibody this invention may comprise combining an PCan065-containing sample with a test antibody and an antibody of this invention to form a mixture, the level of PCan065 antibody bound to PCan065 in the mixture is then determined and compared to the level of PCan065 antibody bound in the mixture to a control mixture, wherein the level of PCan065 antibody binding to PCan065 in the mixture as compared to the control is indicative of the test antibody's binding to an epitope that is bound by the anti-PCan065 antibody of this invention. The level of PCan065 antibody bound to PCan065 is determined by ELISA. The control may be a positive or negative control or both. For example, the control may be a mixture of PCan065, PCan065 antibody of this invention and an antibody known to bind the epitope bound by the PCan065 antibody of this invention. The anti-PCan065 antibody labeled with a label such as those disclosed herein. The PCan065 may be bound to a solid support, e.g., a tissue culture plate or to beads, e.g., SEPHAROSE® beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-PCan065 antibody (full length or fragments) of the invention is conjugated to one or more maytansinoid molecules.

Maytansinoids are mitototic inhibitors which act by inhibiting tubulin polymerization. Maytansine was first isolated from the cast African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DMI linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonoid drug, which could be increased by increasing the number of maytansinoid molecules per antibody molecule. The A7-maytansinoid conjugate showed low systemic cytotoxicity in mice.

Anti-PCan065 Antibody-Maytansinoid Conjugates (Immunoconjugates)

Anti-PCan065 antibody-maytansinoid conjugates are prepared by chemically linking an anti-PCan065 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208, 020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B 1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl (2-pyridyldithio) propionate (SPDP), succinimidyl-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio) propionate (SPDP) (Carlsson et al., Biochem. J. 173:723-737 [1978]) and N-succinimidyl (2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-PCan065 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PCan065 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, 1 5 nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PCan065 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208,020) may be used.

Alternatively, a fusion protein comprising the anti-PCan065 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-PCan065 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-PCan065 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-PCan065 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-PCan065 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-PCan065 antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, oc factor leader (including *Saccharomyces* and *Kluyveromyces* cc-factor leaders), or acid phosphatase leader, the *C albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-PCan065 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-PCan065 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-PCan065 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-PCan065 antibody nucleic acid. Promoters suitable for use with prokaryotic hosts include the phoA promoter, P-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-PCan065 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-PCan065 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human P-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-PCan065 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-PCan065 antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-PCan065 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. lichenifonnis* (e.g., *B. lichenifonnis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-PCan065 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244, 234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated anti-PCan065 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-PCan065 antibody production and cultured in conventional nutrient media modified as appropriate for inducing promoters, selecting transformants, or amplifying the genes encoding the desired sequences.

Culturing Host Cells

The host cells used to produce the anti-PCan065 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-PCan065 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyrollidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-PCan065 antibody which internalizes, it may be desirable to include in the one formulation, an additional antibody, e.g. a second anti-PCan065 antibody which binds a different epitope on PCan065, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–) hydroxybutyric acid.

The formulations to be used for in vivo administration must be sterile. This is readily accomplished by filtration through sterile filtration membranes.

Methods and Treatment Using Anti-PCan065 Antibodies

According to the present invention, the anti-PCan065 antibody that binds to PCan065 or internalizes upon binding to PCan065 on a cell surface is used to treat a subject in need thereof having a cancer characterized by PCan065-expressing cancer cells, in particular, ovarian, breast, colon, prostate, pancreatic or lung cancer, and associated metastases.

The cancer will generally comprise PCan065-expressing cells, such that the anti-PCan065 antibody is able to bind thereto. While the cancer may be characterized by overexpression of the PCan065 molecule, the present application further provides a method for treating cancer which is not considered to be an PCan065-overexpressing cancer.

This invention also relates to methods for detecting cells or tissues which overexpress PCan065 and to diagnostic kits useful in detecting cells or tissues expressing PCan065 or in detecting PCan065 in bodily fluids from a patient. Bodily fluids include blood, serum, plasma, urine, ascites, peritoneal wash, saliva, sputum, seminal fluids, tears, mucous membrane secretions, and other bodily excretions such as stool. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of PCan065 overexpressing cells. A level of PCan065 binding higher than that of such a control sample would be indicative of the test sample containing cells that overexpress PCan065. Alternatively the control may be a sample of cells known to contain cells that overexpress PCan065. In such a case, a level of PCan065 antibody binding in the test sample that is similar to, or in excess of, that of the control sample would be indicative of the test sample containing cells that overexpress PCan065.

Additionally, the methods may comprise combining a test sample with an antibody of this invention, assaying the test sample for antibody binding to PCan065 in the test sample and comparing the level of antibody binding in the test sample to the level of antibody binding in a control sample. A suitable control is, e.g., a non-diseased sample of the same type as the test sample, sample known to be free of PCan065 or a sample of known quantity of PCan065. A level of PCan065 binding higher than that of such a control sample would be indicative of the test sample containing overexpression of PCan065. Alternatively the control may be a sample known to overexpress PCan065. In such a case, a level of PCan065 antibody binding in the test sample that is similar to, or in excess of, that of the control sample would be indicative of the test sample overexpressing PCan065.

PCan065 overexpression may be detected with a various diagnostic assays. For example, over expression of PCan065 may be assayed by immunohistochemistry (IHC). Paraffin embedded tissue sections from a tumor biopsy may be subjected to the IHC assay and accorded an PCan065 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for PCan065 expression may be characterized as not overexpressing PCan065, whereas those tumors with 2+ or 3+ scores may be characterized as overexpressing PCan065.

Alternatively, or additionally, FISH assays such as the INFORM™ (sold by Ventana, Arizona) or PATHVISION™ (VySiS, Illinois) may be carried out on formalin-fixed, paraffin-embedded tumor tissue to determine the extent (if any) of PCan065 overexpression in the tumor. PCan065 overexpression or amplification may be evaluated using an in vivo diagnostic assay, e.g. by administering a molecule (such as an antibody of this invention) which binds PCan065 and which is labeled with a detectable label (e.g. a radioactive isotope or a fluorescent label) and externally scanning the patient for localization of the label.

A sample suspected of containing cells expressing or overexpressing PCan065 is combined with the antibodies of this invention under conditions suitable for the specific binding of the antibodies to PCan065. Binding and/or internalizing the PCan065 antibodies of this invention is indicative of the cells expressing PCan065. The level of binding may be determined and compared to a suitable control, wherein an elevated level of bound PCan065 as compared to the control is indicative of PCan065 overexpression. The sample suspected of containing cells overexpressing PCan065 may be a cancer cell sample, particularly a sample of ovarian, colon, prostate or lung cancer. A serum sample from a subject may also be assayed for levels of PCan065 by combining a serum sample from a subject with an PCan065 antibody of this invention, determining the level of PCan065 bound to the antibody and comparing the level to a control, wherein an elevated level of PCan065 in the serum of the patient as compared to a control is indicative of overexpression of PCan065 by cells in the patient. The subject may have a cancer such as ovarian, colon, prostate or lung cancer.

Currently, depending on the stage of the cancer, ovarian, breast, colon, prostate, pancreatic or lung cancer treatment involves one or a combination of the following therapies: surgery to remove the cancerous tissue, radiation therapy, androgen deprivation (e.g., hormonal therapy), and chemotherapy. Anti-PCan065 antibody therapy may be especially desirable in elderly patients who do not tolerate the toxicity and side effects of chemotherapy well, in metastatic disease where radiation therapy has limited usefulness, and for the management of prostatic carcinoma that is resistant to androgen deprivation treatment. The tumor targeting and internalizing anti-PCan065 antibodies of the invention are useful to alleviate PCan065-expressing cancers, e.g., ovarian, breast, colon, prostate, pancreatic or lung cancers upon initial diagnosis of the disease or during relapse. For therapeutic applications, the anti-PCan065 antibody can be used alone, or in combination therapy with, e.g., hormones, antiangiogens, or radiolabelled compounds, or with surgery, cryotherapy, and/or radiotherapy, notably for ovarian, breast, colon, prostate, pancreatic or lung cancers, also particularly where shed cells cannot be reached. Anti-PCan065 antibody treatment can be administered in conjunction with other forms of conventional therapy, either consecutively with, pre- or post-conventional therapy, Chemotherapeutic drugs such as Taxotere® (docetaxel), Taxol® (paclitaxel), estramustine and mitoxantrone are used in treating metastatic and hormone refractory ovarian, breast, colon, prostate, pancreatic or lung cancer, in particular, in good risk patients. In the present method of the invention for treating or alleviating cancer, in particular, androgen independent and/or metastatic ovarian, breast, colon, prostate or lung cancer, the cancer patient can be administered anti-PCan065 antibody in conjunction with treatment with the one or more of the preceding chemotherapeutic agents. In particular, combination therapy with paclitaxel and modified derivatives (see, e.g., EP0600517) is contemplated. The anti-PCan065 antibody will be administered with a therapeutically effective dose of the chemotherapeutic agent. The anti-PCan065 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-PCan065 antibody conjugated with a cytotoxic agent may be administered to the patient. Preferably, the immunoconjugate bound to the PCan065 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-PCan065 antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-PCan065 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-PCan065 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the PCan065-expressing tumor cells. The cocktail may also comprise antibodies that are directed to other epitopes of PCan065. Preferably the other antibodies do not interfere with the binding and or internalization of the antibodies of this invention.

The antibody therapeutic treatment method of the present invention may involve the combined administration of an anti-PCan065 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetael) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-PCan065 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-PCan065 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-PCan065 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et at., Science 256:808-813 (1992). See also WO 93/25673 and the references cited therein.

Articles of Manufacture and Kits

The invention also relates to an article of manufacture containing materials useful for the detection of PCan065 levels in samples, PCan065 overexpressing cells and/or the treatment of PCan065 expressing cancer, in particular ovarian, breast, colon, prostate, pancreatic or lung cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting PCan065 expressing cells and/or treating a cancer condition and may have a sterile access port (for example the container may be an intravenous solution bag or a vial having a stopper pierceable by a hypodermic injection needle). At least one active agent in the composition is an anti-PCan065 antibody of the invention. The label or package insert indicates that the composition is used for detecting PCan065 levels, PCan065 expressing cells and/or for treating ovarian, breast, colon, prostate, pancreatic or lung cancer, in a patient in need thereof. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for PCan065 cell killing assays, for purification or immunoprecipitation of PCan065 from cells or for detecting the presence of PCan065 in a bodily fluid sample or detecting the presence of PCan065-expressing cells in a cell sample.

For isolation and purification of PCan065, the kit can contain an anti-PCan065 antibody coupled to a solid support, e.g., a tissue culture plate or beads (e.g., SEPHAROSE® beads). Kits can be provided which contain the antibodies for detection and quantitation of PCan065 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below:
PCan065.A4, PCan065.A10, PCan065.A13, PCan065.B1, PCan065.B2, PCan065.B3, PCan065.B4, PCan065.B5, PCan065.B6, PCan065.B7, PCan065.B8, PCan065.B9, PCan065.B10, PCan065.B11, PCan065.B12, PCan065.B13, PCan065.B14, PCan065.B15, PCan065.B16, PCan065.B17, PCan065.B18, PCan065.B19, PCan065.B20, PCan065.B21, PCan065.B22, PCan065.B23, PCan065.B24, PCan065.B25, PCan065.B26, PCan065.B27, PCan065.B28, PCan065.B29, PCan065.B30, PCan065.B31, PCan065.B32, PCan065.B33, PCan065.B34, PCan065.B35, PCan065.B36, PCan065.B37, PCan065.B38, PCan065.B39, PCan065.B40, PCan065.B41, PCan065.B42, PCan065.B43, PCan065.B44, PCan065.B45, PCan065.B46, PCan065.B47, PCan065.B48, PCan065.B101, PCan065.B102, PCan065.B103, PCan065.B104, PCan065.B105, PCan065.B106, PCan065.B107, PCan065.B108, PCan065.B109, PCan065.B110, PCan065.B111, PCan065.B112, PCan065.B113, PCan065.B114, PCan065.B115, PCan065.B116, PCan065.B117 and PCan065.B118.

If the MAb producing hybridoma has been cloned, it will get the nomenclature "X#0.1," e.g., the first clone of PCan065.A10 will be referred to as A10.1, the second clone of A10 will be referred to as A10.2, etc. Sub-clones are designated by a subsequent ".#", e.g. the first sub-clone of PCan065.A10.3 is referred to as A10.1.1, the second sub-clone of A10.1 is A10.1.2, etc. Further generations of sub-clones are annotated in the same format. For the purposes of this invention, a reference to an anti-PCan065 antibody producing hybridoma, e.g. PCan065.A10 or A10, will include all clones and sub-clones of the antibody, e.g., A10.1, A10.2, A10.1.1, etc. Furthermore, the nomenclature PCan065.A10.3, for example, may reference the antibody producing hybridoma, or the antibody itself.

Immunogens and Antigens (Recombinant Proteins, His Tags)

For the PCan065 Constructs described below, nucleic acid molecules encoding regions of PCan065 were inserted into various expression vectors to produce recombinant proteins. These nucleic acid sequences were isolated by PCR using the primers which are routine to design.

For purposes of illustration, the predicted amino acid sequence encoded by each construct is also included. However, the constructs may include naturally occurring variants (e.g. allelic variants, SNPs) within the PCan065 region as isolated by the primers. These variant sequences, and antibodies which bind to them are considered part of the invention as described herein.

PCan065 Construct 1 Sequence and Protein Production

A nucleic acid molecule encoding the mature form of PCan065, Ala197 to Ile308, was inserted into a modified pCMV5His2 vector at the NsiI/NheI sites. Designing primers to isolate a nucleic acid molecule is routine to one of skill in the art.

The modified vector comprises a nucleotide sequence encoding a 17 amino acid secretion signal sequence from human stanniocalcin 1 (STC1) plus 2 transitional amino acids in frame on the 5' side of the insertion site, and a sequence encoding 2 transitional amino acids and a 10 His tag in-frame at the 3' side of the insertion site. The resulting vector with the inserted PCan065 nucleic acid fragment encodes a recombinant PCan065 fusion protein with the STC1 secretion signal fused to the N-terminus and the 10 His-tag fused to the C-terminus of the PCan065 protein fragment (Ala197-Ile308). This recombinant plasmid encoding the PCan065 His-tagged protein is herein referred to as "PCan065 Construct 1". A representative amino acid sequence encoded by PCn065 Construct 1 is presented in SEQ ID NO:1. The PCan065 protein fragment (Ala197-Ile308) in PCan065 Construct 1 is located at Ala20-Ile131 of SEQ ID NO: 1.

```
PCan065 Construct 1 Amino Acid Sequence (SEQ ID NO: 1)
        1          11         21         31         41         51
        |          |          |          |          |          |
      1 MLQNSAVLLV LVISASADIA RNGDHCPLGP GRCCRLHTVR ASLEDLGWAD WVLSPREVQV
     61 TMCIGACPSQ FRAANMHAQI KTSLHRLKPD TVPAPCCVPA SYNPMVLIQK TDTGVSLQTY
    121 DDLLAKDCHC IASHHHHHHH HHH
```

PCan065 Construct 2 Sequence and Protein Production

A nucleic acid molecule encoding the full length of PCan065 (Met1-Ile308), was inserted into a pCMV5His3 vector at the PmeI/NheI site. Designing primers to isolate a nucleic acid molecule is routine to one of skill in the art.

The vector comprises a sequence encoding 2 transitional amino acids and a 10 His tag in-frame at the 3' side of the insertion site. The resulting vector with the inserted PCan065 nucleic acid fragment encodes a recombinant PCan065 fusion protein with the 10 His-tag fused to the C-terminus of the protein. This recombinant plasmid is herein referred to as "PCan065 Construct 2". A representative amino acid sequence encoded by PCan065 Construct 2 is presented in SEQ ID NO:2. The PCan065 protein (Met1-Ile308) in PCan065 Construct 2 is located at Met1-Ile308 of SEQ ID NO: 2.

```
PCan065 Construct 2 Amino Acid Sequence (SEQ ID NO: 2)
         1         11         21         31         41         51
         |          |          |          |          |          |
     1 MPGQELRTLN GSQMLLVLLV LSWLPHGGAL SLAEASRASF PGPSELHSED SRFRELRKRY
    61 EDLLTRLRAN QSWEDSNTDL VPAPAVRILT PEVRLGSGGH LHLRISRAAL PEGLPEASRL
   121 HRALFRLSTP ASRSWDVTRP LRRQLSLARP QAPALHLRLS PPPSQSDQLL AESSSARPQL
   181 ELHLRPQAAR GRRRARARNG DHCPLGPGRC CRLHTVRASL EDLGWADWVL SPREVQVTMC
   241 IGACPSQFRA ANMHAQIKTS LHRLKPDTVP APCCVPASYN PMVLIQKTDT GVSLQTYDDL
   301 LAKDCHCIAS HHHHHHHHHH
```

The recombinant plasmids, PCan065 Construct 1 and PCan065 Construct 2, were used to independently transfect HEK293F cells in suspension culture (1-10 liter serum free medium) in spinner flasks. Culture medium was harvested at 48 hours post-transfection. Medium was concentrated 10-100 fold, and diafiltrated with 20 mM Tris/HCl, 500 mM NaCl, 10% glycerol, pH 7.8. Concentrated medium containing protein encoded by either PCan065 Construct 1 or PCan065 Construct 2 was passed through a 5-mL nickel metal chelating column (His-Select-Ni, Sigma Inc.), which had been previously equilibrated with 50 mM sodium phosphate, 1000 mM NaCl, 10% glycerol, pH 7.8. The column was then washed with 6 column volume (CV) of 50 mM sodium phosphate, 1000 mM NaCl, 20 mM imidazole, 10% glycerol, pH 7.8. Protein encoded by PCan065 Construct 1 and 2 was eluted from the column using 6 CV of 50 mM sodium phosphate, 500 mM NaCl, 10% glycerol, pH 7.7 containing 500 mM imidazole. Samples from collected fractions were subjected to SDS-PAGE and Western blot analysis for assessing the purity of the protein. Purified fractions were pooled and dialyzed against PBS, pH 7.4.

The recombinant protein encoded by PCan065 Construct 1 was alternatively purified and refolded into soluble form by the following procedure. Harvested HEK293F cells (16 grams) expressing PCan065 Construct 1 were lysed in 70 ml of 0.1 M sodium phosphate, pH 8.0, containing 0.4 M NaCl, 10% glycerol and 1% Triton X-100 by sonification and centrifuged at low speed (100-200 RCF). The supernatant was diluted to final volume of 150 ml with the same buffer and mixed with 26.5 ml of 100% ammonium sulfate (15% in final concentration). The solution was centrifuged in a Beckman L8-70M ultracentrifuge with a Ti45 rotor at 24,000 rpm for 30 minutes at 5° C. The precipitation was suspended in 25 ml of 50 mM sodium citrate, pH 5.8, containing 150 mM NaCl by sonification and centrifuged again under the same conditions. The precipitation was dissolved in one ml of 6 M guanidine/HCl and subjected to refolding.

The refolding of the purified PCan065 Construct 1 was carried out by using the protein refolding kit from Pierce Biotechnology, Inc. (Rockford, Ill. 61105). Briefly, 50 μl of the guanidine denatured protein was diluted into 1 ml of each of the refolding buffers (#1-9) following the manufacture's protocol. The mixtures were stirred at 4° C. over two days. After centrifuged at 14,000 rpm for 5 minutes in an eppendorf centrifuge, the supernatants were dialyzed in 4 liters of PBS, pH 7.2, overnight at 4° C. The solutions were recovered and centrifuged again in the same eppendorf centrifuge. The supernatants were pooled and concentrated to 1.2 mg/ml by using a 5 kD cutoff polyethersulfone membrane (VIVASPIN 6, VivaScience, Hannover, Germany).

Cln242 Construct 1 Sequence and Protein Production

A nucleic acid molecule encoding the full length of Cln242 (Met1-Val783), was inserted into a pCMV5His2 vector at the PmeI/NheI site. Designing primers to isolate a nucleic acid molecule is routine to one of skill in the art.

The vector comprises a sequence encoding 6 transitional amino acids and a 10 His tag in-frame at the 3' end of the insertion site. The resulting vector with the inserted Cln242 nucleic acid fragment encodes a recombinant Cln242 fusion protein with the 10 His-tag fused to the C-terminus of the protein. This recombinant plasmid is herein referred to as "Cln242 Construct 1". A representative amino acid sequence encoded by Lng108 Construct 1 is presented in SEQ ID NO:3.

```
Cln242 Construct 1 Amino Acid Sequence
                                                               (SEQ ID NO: 3)
         1         11         21         31         41         51
         |          |          |          |          |          |
     1 MSGGHQLQLA ALWPWLLMAT LQAGFGRTGL VLAAAVESER SAEQKAIIRV IPKLMDPTGK
    61 LNLTLEGVFA GVAEITPAEG KLMQSHPLYL CNASDDDNLE PGFISIVKLE SPRRAPRPCL
   121 SLASKARMAG ERGASAVLFD ITEDRAAAEQ LQQPLGLTWP VVLIWGNDAE KLMEFVYKNQ
   181 KAHVRIELKE PPAWPDYDVW ILMTVVGTIF VIILASVLRI RCRPRHSRPD PLQQRTAWAI
   241 SQLATRRYQA SCRQARGEWP DSGSSCSSAP VCAICLEEFS EGQELRVISC LHEFHRNCVD
   301 PWLHQHRTCP LCMFNITEGD SFSQSLGPSR SYQEPGRRLH LIRQHPGHAH YHLPAAYLLG
   361 PSRSAVARPP RPGPFLPSQE PGMGPRHHRF PRAAHPRAPG EQQRLAGAQH PYAQGWGLSH
   421 LQSTSQHPAA CPVPLRRARP PDSSGSGESY CTERSGYLAD GPASDSSSGP CHGSSSDSVV
   481 NCTDISLQGV HGSSSTFCSS LSSDFDPLVY CSPKGDPQRV DMQPSVTSRP RSLDSVVPTG
   541 ETQVSSHVHY HRHRHHHYKK RFQWHGRKPG PETGVPQSRP PIPRTQPQPE PPSPDQQVTR
   601 SNSAAPSGRL SNPQCPRALP EPAPGPVDAS SICPSTSSLF NLQKSSLSAR HPQRKRRGGP
   661 SEPTPGSRPQ DATVHPACQI FPHYTPSVAY PWSPEAHPLI CGPPGLDKRL LPETPGPCYS
   721 NSQPVWLCLT PRQPLEPHPP GEGPSEWSSD TAEGRPCPYP HCQVLSAQPG SEEELEELCE
   781 QAVMHDIASH HHHHHHHH
```

The recombinant plasmid Cln242 Construct 1 was used to transfect HEK 293F cells in suspension culture (1-10 liter serum free medium) in a bioreactor. Culture medium was harvested at 48 hours post-transfection. Medium was concentrated 10-100 fold, and diafiltrated with 20 mM Tris/HCl, 500 mM NaCl, 5% glycerol, pH 7.8. Concentrated medium containing protein encoded by Cln242 Construct 1 was passed through a 10-mL nickel metal chelating column (His-Select-Ni, Sigma Inc.), which had been previously equilibrated with 50 mM sodium phosphate, 500 mM NaCl, 5% glycerol, pH 8.0. The column was then washed with 7 column volume (CV) of 50 mM sodium phosphate, 500 mM NaCl, 20 mM imidazole, 10% glycerol, pH 8.0. Protein encoded by Cln242 Construct 1 was eluted from the column using 9 CV of 50 mM sodium phosphate, 500 mM NaCl, 10% glycerol, pH 7.6 containing 50 mM imidazole and 10 CV of 50 mM sodium phosphate, 500 mM NaCl, 10% glycerol, pH 7.6 containing 100 mM imidazole. Samples from collected fractions were subjected to SDS-PAGE and Western blot analysis for assessing the purity of the protein. Purified fractions were pooled and concentrated.

Cln101 Construct 1 Sequence and Protein Production

A nucleic acid molecule encoding the mature form of Cln101, Asp23 to Pro158, was inserted into a modified pCMV5His2 vector at the NsiI/NheI sites. Designing primers to isolate a nucleic acid molecule is routine to one of skill in the art.

The modified vector comprises a nucleotide sequence encoding a 23 amino acid secretion signal sequence from human stanniocalcin 1 (STC1) plus 4 transitional amino acids in frame on the 5' side of the insertion site, and a sequence encoding 2 transitional amino acids and a 10 His tag in-frame at the 3' side of the insertion site. The resulting vector with the inserted Cln101 nucleic acid fragment encodes a recombinant Cln101 fusion protein with the STC1 secretion signal fused to the N-terminus and the 10 His-tag fused to the C-terminus of the Cln101 protein fragment (Asp23-Pro158). This recombinant plasmid encoding the Cln101 His-tagged protein is herein referred to as "Cln101 Construct 1". A representative amino acid sequence encoded by Cln101 Construct 1 is presented in SEQ ID NO:4.

```
Cln101 Construct 1 Amino Acid Sequence (SEQ ID NO: 4)
     1         11         21         31         41         51
     |          |          |          |          |          |
   1 MLQNSAVLLV LVISASATHE AEQSRMHDII MRPSCAPGWF YHKSNCYGYF RKLRNWSDAE
  61 LECQSYGNGA HLASILSLKE ASTIAEYISG YQRSQPIWIG LHDPQKRQQW QWIDGAMYLY
 121 RSWSGKSMGG NKHCAEMSSN NNFLTWSSNE CNKRQHFLCK YRPASHHHHH HHHHH
```

The recombinant plasmid Cln101 Construct 1 was used to transfect HEK 293F cells in suspension culture (1-10 liter serum free medium) in a bioreactor. Culture medium was harvested at 48 hours post-transfection. Medium was concentrated 10-100 fold, and diafiltrated with 20 mM Tris/HCl, 500 mM NaCl, 5% glycerol, pH 7.8. Concentrated medium containing protein encoded by Cln101 Construct 1 was passed through a 10-mL nickel metal chelating column (His-Select-Ni, Sigma Inc.), which had been previously equilibrated with 50 mM sodium phosphate, 500 mM NaCl, 5% glycerol, pH 8.0. The column was then washed with 7 column volume (CV) of 50 mM sodium phosphate, 500 mM NaCl, 20 mM imidazole, 10% glycerol, pH 8.0. Protein encoded by Lng108 Construct 1 was eluted from the column using 9 CV of 50 mM sodium phosphate, 500 mM NaCl, 10% glycerol, pH 7.6 containing 50 mM imidazole and 10 CV of 50 mM sodium phosphate, 500 mM NaCl, 10% glycerol, pH 7.6 containing 100 mM imidazole. Samples from collected fractions were subjected to SDS-PAGE and Western blot analysis for assessing the purity of the protein. Purified fractions were pooled and concentrated.

Immunization

Eight BALB/c mice were immunized intradermally in both rear footpads with PCan065 Construct 1 (A-series antibodies) or PCan065 Construct 2 (B-series antibodies). All injections were 25 uL per foot. The first injection of 10 ug of antigen per mouse was in Dulbecco's phosphate buffered saline (DPBS) mixed in equal volume to volume ratio with Titermax gold adjuvant (Sigma, Saint Louis, Miss.). Subsequently, mice were immunized twice weekly for 5 weeks. For the 2nd through 10th injection, mice were immunized with 10 ug of antigen in 20 uL of DPBS plus 5 uL of Adju-phos adjuvant (Accurate Chemical & Scientific Corp., Westbury, N.Y.) per mouse. The final immunization consisted of 10 ug antigen diluted in DPBS alone.

Hybridoma Fusion

Four days after the final immunization, mice were sacrificed and draining lymph node (popliteal) tissue was collected by sterile dissection. Lymph node cells were dispersed using a Tenbroeck tissue grinder (Wheaton #347426, VWR, Brisbane, Calif.) followed by pressing through a sterile sieve (VWR) into DMEM and removing T-cells via anti-CD90 (Thy1.2) coated magnetic beads (Miltenyi Biotech, Bergisch-Gladbach, Germany).

These primary B-cell enriched lymph node cells were then immortalized by electro-cell fusion (BTX, San Diego, Calif.) with the continuous myeloma cell line P3x63Ag8.653 (Kearney, J. F. et al., J. Immunology 123: 1548-1550, 1979). The myeloma and B-cells were pooled at a 1:1 ratio for the fusion. These fusion cultures were distributed at 2 million cells per plate into wells of 96 well culture plates (Costar #3585, VWR). The remainder of the cells was cultured in bulk in HAT selection medium for 10 days and cryopreserved for future screens. Successfully fused cells were selected by culturing in selection medium (DMEM/15% FBS) containing 2.85 µM Azaserine, 50 µM Hypoxanthine (HA) (Sigma) or 50 µM Hypoxanthine, 0.2 µM Aminopterin, 8 µM Thymidine (HAT) (Sigma) supplemented with recombinant human IL-6 (Sigma) at 0.5 ng/mL. Cultures were transitioned into medium (DMEM/10% FBS) without selection and IL-6 supplements for continued expansion and antibody production.

Supernatants from wells were screened by enzyme linked solid phase immunoassay (ELISA). Monoclonal cultures, consisting of the genetically uniform progeny from single cells, were established after the screening procedure, by sorting of single viable cells into wells of two 96 well plates, using flow cytometry (Coulter Elite; Beckman-Coulter, Miami, Fla.). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

Direct ELISA Screening & Selection of Hybridomas Producing PCan065 Specific Antibodies PCan065 A-Series MAbs Hybridoma cell lines were selected for production of PCan065 specific antibody by direct ELISA. Wells were coated with either PCan065 Construct 1 or Cln242 Construct 1 as negative control. One ug/mL protein in PBS (100 uL/well) was incubated overnight in 96 well polystyrene EIA plates (Costar #9018, VWR) at 4° C. The plate wells were washed twice with Tris buffered saline with 0.05% Tween20, pH 7.4 (TBST). Nonspecific binding capacity was blocked by filling the wells (300 ul/well) with TBST/0.5% bovine serum albumin (TBST/BSA) and incubating for >30 minutes at room temperature (RT). The wells were emptied and filled with 50 uL/well TBST/BSA to prevent them from drying out during the sample collection process. Hybridoma culture medium sample (50 uL) was added to the wells and incubated for 1 hour at RT. The wells were washed 3 times with TBST. One hundred uL of alkaline phosphatase conjugated goat anti-mouse IgG (Fc) with minimal cross-reactivity to human Fc (P/N115-055-071, Jackson Immunoresearch), diluted 1:5000 in TBST/BSA, was added to each well and incubated for >1 hour at RT. The wells were washed 3 times with TBST. One hundred uL of alkaline phosphatase substrate para-nitrophenylphosphate (pNPP) (Sigma) at 1 mg/mL in 1 M Diethanolamine buffer pH 8.9 (Pierce) was added to each well and incubated for 20 min at RT. The enzymatic reaction was quantified by measuring the solution's absorbance at 405 nm wavelength.

Supernatants from three hybridomas produced an absorbance value of greater than 0.4 in wells coated with PCan065 Construct 1 and less than 0.1 in wells coated with Cln242 Construct 1, indicating specific binding to PCan065. These hybridomas, named PCan065.A4, PCan065.A10 and PCan065.A13, were expanded and cryopreserved.

PCan065 B-Series MAbs

ELISA screens of hybridoma supernatants were performed as described for the A-series, except that wells were coated with PCan065 Construct 2 and Cln01 Construct 1. Supernatants from ninety-four hybridomas produced an absorbance value of greater than 0.50 in wells coated with PCan065 Construct 1 and less than 0.11 in wells coated with Cln101 Construct 1, indicating specific binding to PCan065. Forty eight hybridomas with the highest signal-to-noise ratio, named PCan065.B1 to PCan065.B48, were expanded and cryopreserved.

Cryopreserved fusion cultures from the B-series fusion were thawed, cultured for about 2 weeks and plated at 1 cell/well into 96 well plates by single cell sorting (Beckman Coulter Elite). After about 2 weeks supernatants were screened by direct ELISA against recombinant human GDF-15/MIC-1 (R&D Systems, Minneapolis, Minn.). Supernatants form eighteen hybridomas produced an absorbance value of greater than 1.0 in wells coated with GDF-15/MIC-1 and less than 0.1 in wells coated with a nonrelevant protein, indicating specific binding to PCan065. These hybridomas, named PCan065.B101.1 to B118.1, were expanded and cryopreserved.

Cloning of Hybridomas Producing PCan065 Specific MAb

Based on the ELISA data above, the following hybridomas were expanded and selected for single cell cloning into 96 well culture plates by cell sorting (Coulter Elite): PCan065.A10, PCan065.B1, PCan065.B2, PCan065.B3, PCan065.B4, PCan065.B5, PCan065.B16, PCan065.B27 and PCan065.B29. After 2 weeks of culture, supernatants of each subclone were tested by direct ELISA on wells coated with PCan065 Construct 2. Three ELISA-positive subclones per parent hybridoma were expanded and cryopreserved.

Off-Ranking Analysis of PCan065 Hybridoma Supernatants

Dissociation constants (kd) were calculated from surface plasmon resonance measurements using a BIACORE 3000 instrument (BiaCore, Piscataway, N.J.). A RAM-Fc surface was used to capture each antibody supernatant, followed by an injection of the protein encoded by a PCan065 Construct over the captured antibody.

Flow cell 1 of a CM5 sensor chip (BiaCore) was used as a blank surface for reference subtractions, and was activated and then inactivated with ethanolamine per standard BiaCore protocols. Flow cell 2 was used to immobilize RAM Fc using an injection time of 12 minutes and a flow of 5 ul/min. The RAM-Fc (BiaCore) was diluted to 35 ug/mL in 10 mM acetate as suggested. Standard amine coupling (BiaCore) was used to immobilize 10349 RU. Hybridoma supernatants were diluted 1:2 in HBS-EP running buffer (BiaCore) and passed over flow cells 1 and 2. Antibodies were captured at 5 ul/min flow rate, 3 minute injection, and a PCan065 Construct protein was injected at 5 ug/mL for 2 minutes. The dissociation time was 3 minutes. The regeneration of the chip surface, or removal of captured hybridoma supernatants binding to the antigen between cycles, was performed by injecting 10 mM glycine pH 1.75 for 30 seconds at 100 uL/minute.

The above procedure was performed by using the BiaCore's surface preparation and binding wizard included in the BiaCore control software. Results were automatically fitted using the separate ka/kd function included in the BiaCore analysis software, assuming a 1:1 Langmuir binding model. Results in Table 1a below include the antibody producing hybridoma, the response units of Mab binding (Mab RU) and antigen binding (antigen RU), and the dissociation constant (kd).

TABLE 1a

PCan065 MAb Kinetics

| Clone | Mab RU | Antigen RU | kd |
| --- | --- | --- | --- |
| A10.3 | 2413 | 721 | 3.40E−04 |
| B1.1 | 1832 | 301 | 2.40E−04 |
| B2.2 | 1163 | 1528 | 1.12E−04 |
| B3.1 | 1327 | 237 | 3.66E−04 |
| B4.1 | 812 | 357 | 1.73E−04 |
| B5.3 | 1057 | 1240 | 2.02E−04 |
| B16.2 | 727 | 371 | 1.57E−04 |
| B27.1 | 1308 | 394 | 2.62E−04 |

PCan065 MAb Isotypes

The isotypes of 2 anti-PCan065 MAbs were determined using commercially available mouse monoclonal antibody isotyping immunoassay test kits (IsoStrip, Roche Diagnostic Corp., Indianapolis, Ind.). Isotypes are listed in Table 1b.

TABLE 1b

PCan065 MAb Isotypes

| Clone | Isotype |
| --- | --- |
| PCan065.A10.3 | IgG2b kappa |
| PCan065.B2.2 | IgG1 kappa |

Direct ELISA of Purified PCan065 Specific MAb

Purified antibodies from cloned hybridomas were tested for binding efficacy by direct ELISA against PCan065 as described above. The PCan065 antibodies evaluated include PCan065.A10, PCan065.B1, PCan065.B2, PCan065.B3, PCan065.B4, PCan065.B5, PCan065.B16, PCan065.B27 and PCan065.B29. These antibodies were tested by direct ELISA on wells coated with recombinant human GDF-15/MIC-1 from R&D Systems (Minneapolis, Minn.) at varying concentrations (listed in Table 2A and 2B below). The antibodies were tested as both biotinylated and non-biotinylated forms. Tables 2A and 2B list the absorbance for each antibody as measured with a SpectroMax 190 instrument at 450 OD.

TABLE 2A

Direct ELISA with purified Anti-PCan065 MAb

Concentration of GDF-15/MIC-1 protein (ug/mL)

| MAb | 10 | 5 | 2.5 | 1.25 | 0.625 | 0.313 | 0.156 | 0 |
|---|---|---|---|---|---|---|---|---|
| PCan065.A10.3 | 0.286 | 0.262 | 0.184 | 0.189 | 0.166 | 0.144 | 0.120 | 0.066 |
| PCan065.B1.1  | 0.057 | 0.054 | 0.067 | 0.054 | 0.056 | 0.054 | 0.051 | 0.054 |
| PCan065.B2.2  | 0.965 | 0.898 | 0.771 | 0.629 | 0.502 | 0.355 | 0.218 | 0.053 |
| PCan065.B3.1  | 0.082 | 0.066 | 0.058 | 0.055 | 0.055 | 0.053 | 0.053 | 0.053 |
| PCan065.B4.1  | 0.082 | 0.070 | 0.061 | 0.058 | 0.055 | 0.057 | 0.052 | 0.052 |
| PCan065.B5.3  | 0.055 | 0.052 | 0.051 | 0.053 | 0.054 | 0.052 | 0.055 | 0.052 |
| PCan065.B16.2 | 0.087 | 0.079 | 0.062 | 0.060 | 0.055 | 0.051 | 0.052 | 0.051 |
| PCan065.B27.1 | 0.185 | 0.166 | 0.137 | 0.118 | 0.096 | 0.082 | 0.077 | 0.039 |
| PCan065.B29.2 | 0.094 | 0.077 | 0.066 | 0.058 | 0.054 | 0.053 | 0.050 | 0.049 |

TABLE 2B

Direct ELISA with purified biotinylated Anti-PCan065 MAb

Concentration of GDF-15/MIC-1 protein (ug/mL)

| MAb | 10 | 5 | 2.5 | 1.25 | 0.625 | 0.313 | 0.156 | 0 |
|---|---|---|---|---|---|---|---|---|
| PCan065.A10.3 | 2.743 | 2.319 | 1.695 | 1.346 | 1.008 | 0.808 | 0.615 | 0.058 |
| PCan065.B1.1  | 0.210 | 0.145 | 0.108 | 0.090 | 0.066 | 0.074 | 0.065 | 0.245 |
| PCan065.B2.2  | 4.000 | 3.789 | 4.000 | 3.138 | 2.149 | 1.679 | 1.100 | 0.069 |
| PCan065.B3.1  | 0.264 | 0.158 | 0.118 | 0.091 | 0.078 | 0.070 | 0.069 | 0.060 |
| PCan065.B4.1  | 0.526 | 0.338 | 0.218 | 0.144 | 0.104 | 0.082 | 0.072 | 0.062 |
| PCan065.B5.3  | 0.139 | 0.107 | 0.078 | 0.071 | 0.063 | 0.062 | 0.064 | 0.059 |
| PCan065.B16.2 | 0.511 | 0.361 | 0.231 | 0.172 | 0.120 | 0.088 | 0.073 | 0.058 |
| PCan065.B27.1 | 1.317 | 1.136 | 0.903 | 0.687 | 0.518 | 0.402 | 0.279 | 0.067 |
| PCan065.B29.2 | 0.472 | 0.333 | 0.227 | 0.148 | 0.110 | 0.135 | 0.097 | 0.099 |

PCan065 A and B-Series Mab Checkerboard ELISA

A checkerboard ELISA was ran with PCan065 antibodies above, a polyclonal GDF-15/MIC-1 antibody from R&D Systems (Minneapolis, Minn.) and a monoclonal antibody Cln248 as a negative control.

High binding polystyrene plates (Corning Life Sciences) were coated overnight at 4° C. with 0.3 µg/well of a first anti-PCan065 MAb. The coating solution was aspirated off and free binding sites were blocked with 300 µl/well Superblock-TBS (Pierce Biotechnology, Illinois) on a shaker for 1 hour at room temperature (RT). After washing 4 times with washing buffer (TBS+0.05% Tween20), 80 µl of Assay Buffer (TBS, 1% BSA, 1% Mouse Serum, 1% Calf Serum, and 0.1% ProClin™) was added to each well, followed by 20 µl of antigen per well. The plate was incubated for 60 minutes on a shaker. For each sandwich ELISA, standards of specified concentrations of recombinant human mature form GDF-15/MIC-1 (R&D Systems, Minneapolis, Minn.) were run in parallel with test samples. Standards and test samples were diluted in Assay Buffer. For detection, 100 µl of a second biotinylated MAb (0.15 µg/ml) was added to each well and incubated for 1 hour at room temperature (RT), while shaking. After washing, 100 µL of Streptavidin-HRP conjugate (Jackson Lab) at 1:80,000 dilution in TBS, was added to each well. Plates were then incubated with shaking at RT for 30 min. After washing the plate, 100 uL/well of TMB-Stable Stop substrate (Moss, Inc.) was added to each well and the plate was incubated at RT, covered and on the shaker for 15 minutes. The reaction was stopped using 100 µl/well 1N HCl, and the plates were read at 450 nm using a Spectramax 190 plate reader (Molecular Devices).

PCan065 A and B-Series MAb ELISA Pairing Results

The results of the checkerboard ELISAs on anti-PCan065 MAbs are shown in Tables 3a and 3b below. Each antibody was tested as both a coating and detecting antibody, in all possible combinations. All pairs were tested with 10 ng/ml of recombinant human GDF-15/MIC-1 (mature form) in buffer or with buffer alone as a blank (negative control). A non binding Cln248 MAb was also used as a negative control. The results in table 3a below are shown as specific signal/noise ratio. Capturing MAbs are listed on the Y-axis with detecting MAbs on the X-axis.

TABLE 3a

Pairing of PCan065 A and B-series MAb by Sandwich ELISA

| | | detecting 2° MAb | | | | | | | | | | |
|---|---|---|---|---|---|---|---|---|---|---|---|---|
| | | A10.3 | B1.1 | B2.2 | B3.1 | B4.1 | B5.3 | B16.2 | B27.1 | B29.2 | GDF15 Poly | Cln248 MAb |
| coating 1° MAb | A10.3 | 1 | 1 | 18 | 2 | 2 | 1 | 2 | 1 | 1 | 18 | 1 |
| | B1.1 | 1 | 1 | 1 | 1 | 1 | 1 | 1 | 1 | 1 | 1 | 1 |
| | B2.2 | 25 | 1 | 3 | 1 | 2 | 1 | 2 | 20 | 2 | 11 | 1 |
| | B3.1 | 1 | 1 | 3 | 1 | 1 | 1 | 1 | 1 | 1 | 8 | 1 |
| | B4.1 | 4 | 1 | 2 | 1 | 1 | 4 | 2 | 1 | 3 | 3 | 1 |

TABLE 3a-continued

Pairing of PCan065 A and B-series MAb by Sandwich ELISA

|  | detecting 2° MAb | | | | | | | | | | |
|---|---|---|---|---|---|---|---|---|---|---|---|
|  | A10.3 | B1.1 | B2.2 | B3.1 | B4.1 | B5.3 | B16.2 | B27.1 | B29.2 | GDF15 Poly | Cln248 MAb |
| B5.3 | 1 | 1 | 1 | 1 | 1 | 1 | 1 | 1 | 1 | 2 | 2 |
| B16.2 | 3 | 1 | 2 | 1 | 1 | 1 | 1 | 2 | 1 | 2 | 1 |
| B27.1 | 5 | 1 | 61 | 10 | 4 | 2 | 5 | 1 | 5 | 9 | 2 |
| B29.2 | 2 | 1 | 3 | 1 | 1 | 1 | 1 | 2 | 1 | 2 | 1 |
| Cln248 | 1 | 1 | 1 | 1 | 1 | 1 | 1 | 1 | 1 | 1 | 1 |

In a second checkerboard ELISA additional anti-PCan065 MAbs were evaluated for pairing as above. Results in Table 3b below are shown as a specific signal/noise ratio. Capturing MAbs are listed on the Y-axis with detecting MAbs on the X-axis.

TABLE 3a

Pairing of PCan065 A and B-series MAb by Sandwich ELISA

|  |  | detecting 2° Mab | | | | | | | | | | |
|---|---|---|---|---|---|---|---|---|---|---|---|---|
|  |  | B2.2 | B102 | B111 | A10.1 | B101 | B104 | B106 | B108 | B114 | B27.1 | B110 |
| coating 1° MAb | B2.2 | 3 | 6 | 4 | 15 | 5 | 8 | 9 | 29 | 8 | 22 | 4 |
|  | B102 | 2 | 2 | 1 | 19 | 5 | 33 | 36 | 22 | 34 | 2 | 5 |
|  | B111 | 3 | 1 | 2 | 29 | 11 | 37 | 54 | 34 | 52 | 18 | 11 |
|  | A10.1 | 50 | 50 | 49 | 2 | 2 | 2 | 2 | 2 | 2 | 2 | 2 |
|  | B101 | 71 | 81 | 76 | 1 | 1 | 1 | 1 | 1 | 1 | 1 | 1 |
|  | B104 | 42 | 50 | 52 | 1 | 1 | 1 | 1 | 1 | 1 | 1 | 1 |
|  | B106 | 76 | 64 | 59 | 1 | 1 | 2 | 1 | 2 | 1 | 1 | 1 |
|  | B108 | 45 | 26 | 31 | 1 | 1 | 1 | 1 | 1 | 1 | 1 | 1 |
|  | B114 | 75 | 75 | 71 | 1 | 1 | 1 | 1 | 1 | 1 | 1 | 1 |
|  | B27.1 | 76 | 74 | 58 | 1 | 1 | 2 | 1 | 1 | 2 | 1 | 1 |
|  | B110 | 29 | 27 | 18 | 1 | 1 | 1 | 1 | 1 | 1 | 1 | 1 |
|  | B112 | 81 | 54 | 52 | 1 | 1 | 2 | 1 | 2 | 1 | 1 | 1 |
|  | B113 | 11 | 13 | 10 | 1 | 1 | 1 | 1 | 1 | 1 | 1 | 1 |
|  | B115 | 80 | 67 | 67 | 1 | 1 | 2 | 1 | 1 | 1 | 1 | 1 |
|  | B116 | 43 | 48 | 39 | 1 | 1 | 1 | 1 | 1 | 1 | 1 | 1 |
|  | B3.1 | 5 | 5 | 5 | 1 | 1 | 1 | 1 | 1 | 1 | 1 | 1 |
|  | B1.1 | 1 | 1 | 1 | 1 | 1 | 1 | 1 | 1 | 1 | 1 | 1 |
|  | B4.1 | 2 | 2 | 1 | 2 | 1 | 1 | 1 | 2 | 1 | 1 | 1 |
|  | B5.3 | 1 | 1 | 2 | 1 | 1 | 1 | 1 | 1 | 1 | 1 | 1 |
|  | B16.2 | 2 | 2 | 1 | 1 | 1 | 1 | 1 | 1 | 1 | 1 | 1 |
|  | B29.2 | 3 | 4 | 3 | 1 | 1 | 1 | 1 | 1 | 1 | 1 | 1 |
|  | Cln248 | 1 | 1 | 1 | 1 | 1 | 1 | 1 | 1 | 1 | 1 | 1 |

|  |  | detecting 2° Mab | | | | | | | | |
|---|---|---|---|---|---|---|---|---|---|---|
|  |  | B113 | B115 | B116 | B3.1 | B1.1 | B4.1 | B5.3 | B16.2 | B29.2 | Cln248 |
| coating 1° MAb | B2.2 | 4 | 4 | 3 | 1 | 1 | 2 | 1 | 3 | 5 | 1 |
|  | B102 | 5 | 4 | 4 | 1 | 1 | 1 | 1 | 1 | 1 | 1 |
|  | B111 | 10 | 10 | 7 | 1 | 1 | 1 | 1 | 2 | 2 | 1 |
|  | A10.1 | 2 | 2 | 2 | 3 | 2 | 2 | 2 | 2 | 3 | 2 |
|  | B101 | 2 | 1 | 1 | 3 | 1 | 1 | 1 | 1 | 1 | 1 |
|  | B104 | 1 | 1 | 1 | 2 | 1 | 1 | 1 | 1 | 2 | 1 |
|  | B106 | 2 | 1 | 1 | 2 | 1 | 2 | 1 | 2 | 2 | 1 |
|  | B108 | 1 | 1 | 1 | 1 | 1 | 4 | 1 | 3 | 3 | 1 |
|  | B114 | 1 | 1 | 1 | 2 | 1 | 2 | 1 | 2 | 1 | 1 |
|  | B27.1 | 2 | 1 | 1 | 7 | 1 | 3 | 2 | 3 | 2 | 1 |
|  | B110 | 1 | 1 | 1 | 2 | 1 | 1 | 1 | 1 | 1 | 1 |
|  | B112 | 2 | 1 | 1 | 3 | 1 | 2 | 1 | 2 | 2 | 1 |
|  | B113 | 1 | 1 | 1 | 1 | 1 | 1 | 1 | 1 | 1 | 1 |
|  | B115 | 2 | 1 | 1 | 3 | 1 | 1 | 1 | 1 | 1 | 1 |
|  | B116 | 1 | 1 | 1 | 2 | 1 | 1 | 1 | 1 | 1 | 1 |
|  | B3.1 | 1 | 1 | 1 | 1 | 1 | 1 | 1 | 1 | 1 | 1 |
|  | B1.1 | 1 | 1 | 1 | 1 | 1 | 1 | 1 | 1 | 1 | 1 |
|  | B4.1 | 1 | 1 | 1 | 1 | 1 | 1 | 1 | 1 | 1 | 1 |
|  | B5.3 | 1 | 1 | 1 | 1 | 1 | 1 | 1 | 1 | 1 | 1 |
|  | B16.2 | 1 | 1 | 1 | 1 | 1 | 1 | 1 | 1 | 1 | 1 |
|  | B29.2 | 1 | 1 | 1 | 1 | 1 | 1 | 1 | 1 | 1 | 1 |
|  | Cln248 | 1 | 1 | 1 | 1 | 1 | 1 | 1 | 1 | 1 | 1 |

The signal/noise ratios recorded are relative to each ELISA experiment. Therefore, data in Tables 3a and 3b demonstrate which MAbs pair well to detect PCan065 compared to others MAb pairs evaluated. Absolute values should not be compared between Tables 3a and 3b. Results from the ELISA pairing demonstrate that the anti-PCan065 MAbs detect several distinct epitopes. The GDF-15 polyclonal antibody from R&D Systems bound GDF-15 indiscriminately in the assays represented in the checkerboard. In contrast, monoclonal antibodies PCan065.A10, PCan065.B1, PCan065.B2, PCan065.B3, PCan065.B4, PCan065.B5, PCan065.B16, PCan065.B27 and PCan065.B29 had specific binding patterns in the assays represented in the checkerboard, demonstrating unique binding epitopes. An epitope map of the PCan065 MAbs derived from the pairing results is shown in FIG. 1. Antibodies PCan065.B1 and PCan065.B5 detected the full length GDF-15 protein. Antibody pairs with the highest signal/noise ratio were selected to test sensitivity for recombinant protein, reactivity towards native protein in cell lines and serum samples.

PCan065 Sandwich ELISA Format and Standard Curve

In the screening and pairing assays above, anti-PCan065 antibody pair (capture/detect) A10.3/B2.2 demonstrated high specificity and excellent sensitivity for the detection of PCan065. These antibody pairs were selected for use in a sandwich ELISA for detection of PCan065.

For the A10.3/B2.2 ELISA pair GDF15/MIC-1 (R&D Systems) standards were run at concentrations of 6, 2, 0.75, 0.3, 0.05, and 0 ng/ml in parallel with the samples. A sensitive detection system based on the use of horseradish peroxidase (HRP) (1:80,000 dilution) and high sensitivity TMB-Stable Stop substrate (MOSS) was used evaluations below. An alternative assay format with a sensitive alkaline phosphatase (AP) detection system may be used. The AP system is based on the use of alkaline phosphatase and p-Nitrophenyl phosphate (pNNP) substrate. In either assay format the development enzyme (HRP or AP) may be directly conjugated to the B2.2 detection antibody for simplicity of the ELISA procedure.

Figure 2:
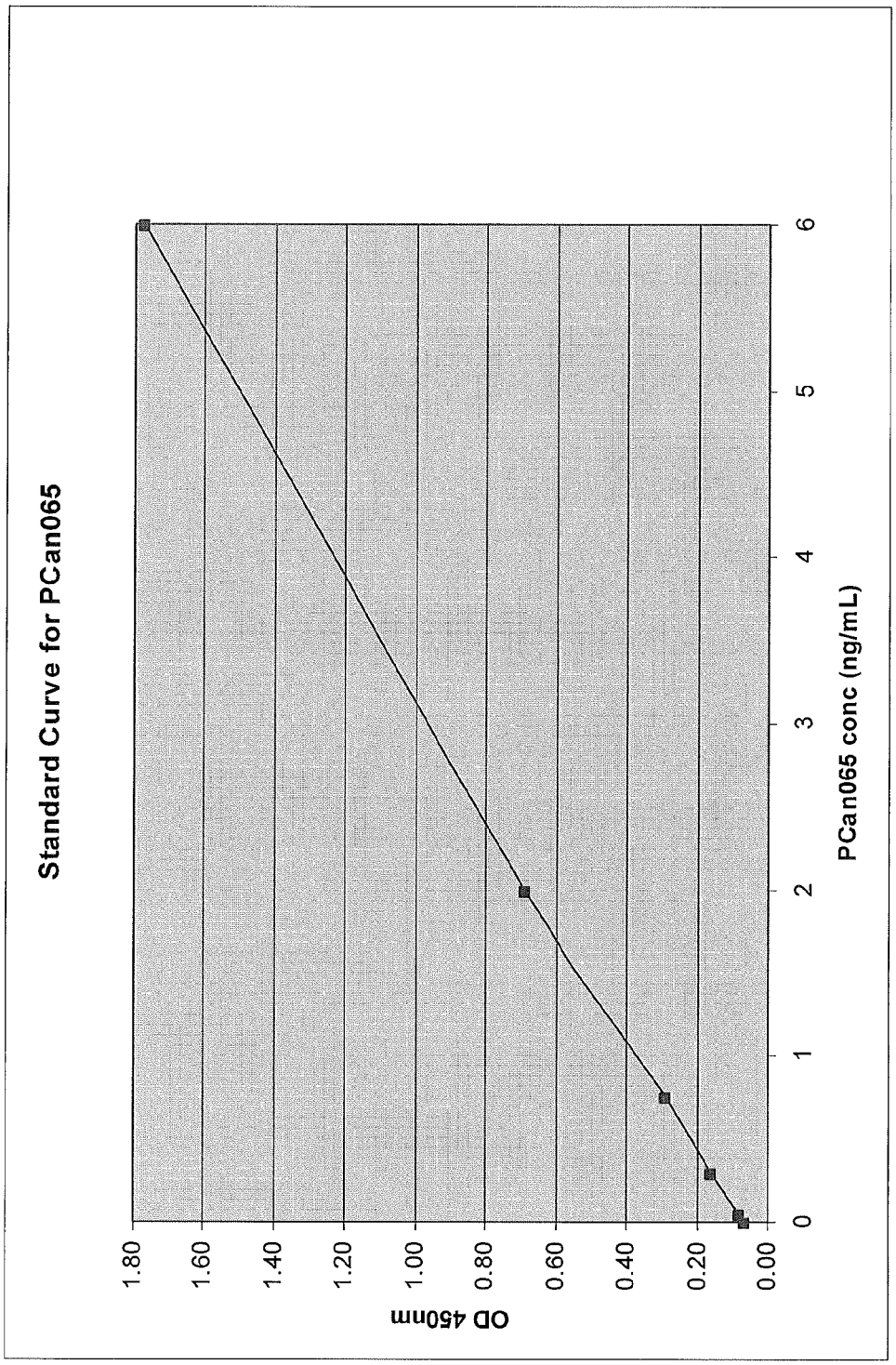
FIG. 2 shows the PCan065 A10.3/B2.2 ELISA Standard Curve.

The minimal detectable dose (MDD) for PCan065 in the ELISA format, A10.3/B2.2, was determined to be 0.015 ng/ml. For calculation of median values, samples with values below the MDD were defined as MDD. The MDD is defined as two standard deviations above the background signal. A standard curve for the A10.3/B2.2 assay format is depicted in FIG. 2. This assay can accurately quantify PCan065 (MIC-1) in the range of about 0.015-6 ng/mL. This assay has a greater detection range and lower end sensitivity than other MIC-1 ELISAs, which have a quantification rage of about 20-900 pg/mL or 0.020-0.9 ng/mL (see Moore et al. J Clin Endocrinol Metab. 2000 December; 85(12):4781-8).

Example 2

Monoclonal Sandwich ELISA Detection of PCan065 in Human Serum Samples

Human Serum Samples

Human cancer and benign serum samples were obtained from IMPATH-BCP, Inc. (Franklin, Mass.), Diagnostic Support Services, Inc. (West Yarmouth, Mass.) and ProteoGenex (Culver City, Calif.). The serum samples from healthy men and women were obtained from ProMedDx LLC (Norton, Mass.). All samples were aliquoted upon arrival and stored at minus 80° C. until use.

The concentration of PCan065 was measured in more than 2228 serum samples from normal/healthy individuals, individuals with lung, breast, colon, prostate or ovarian cancer and individuals with non-cancerous, benign diseases. Benign diseases are grouped by tissue type and include: A. Hyperplasia, Fibroadenoma, and Fibrocystic Breasts for Breast; Crohn's, Diverticulitis, Ulcerative Colitis, and Polyps for Colon; Asthma, Chronic Bronchitis, Emphysema, Interstitial Lung Disease, and Pulmonary Hypertension for Lung; Endometriosis, Enlarged Ovaries, and Polycystic Ovaries for Ovarian; Benign Prostatic Hyperplasia, Prostatic Intraepithelial Neoplasia, and Prostatitis for Prostate. An overview of all samples tested is listed in the table 4 below.

TABLE 4

Summary of serum samples:

| Sample Type | No. of Samples Tested | No. of Samples in Analysis |
| --- | --- | --- |
| Normal | 594 (285-F, 309-M) | 565 (274-F, 291-M) |
| Breast Cancer | 150 | 145 |
| Breast Benign | 180 | 168 |
| Colon Cancer | 125 | 122 |
| Colon Benign | 60 | 56 |
| Lung Cancer | 198 | 191 |
| Lung Benign | 248 | 239 |
| Ovarian Cancer | 97 | 97 |
| Ovarian Benign | 276 | 261 |
| Prostate Cancer | 156 | 152 |
| Prostate Benign | 144 | 140 |

It has been previously shown that a polymorphism in the MIC-1 gene alters the histidine to an aspartic acid (MIC-1 H and MIC-1 D) at position 6 of the mature protein. See Brown et al., Biotechniques. 2002 July; 33(1):118-20, 122, 124 passim. A small portion (4%) of the sample population in Table 4 was undetectable by the PCan065 A10.3/B2.2 ELISA which is in agreement with the differing phenotypes resulting for this polymorphism. Only samples with PCan065 values above the ELISA MDD (0.015 ng/mL) are reported and evaluated below.

Detection of PCan065 in Serum with Sandwich ELISAs

In the following tables demonstrating detection of PCan065 in serum, samples are grouped by type and identified by tissue and disease state of the tissue. Tissue annotation includes: BR=Breast, CN=Colon, LN=Lung, OV=Ovarian, and PR=Prostate. Disease states may be specifically indicated or abbreviated into groups as: CAN=Cancer and BEN=Benign. Samples from non-diseased men and women are annotated as NRM Male (NRM M) and NRM Female (NRM F), respectively. For example, BR CAN indicates breast cancer samples and CN BEN indicates benign colon disease samples.

Benign Diseases are abbreviated as: A. Hyperplasia (AHYP), Fibroadenoma (FBAD), Fibrocystic Breasts (FBCY), Crohn's (CHRN), Diverticulitis (DVCT), Ulcerative Colitis (UCOL), Polyps (PLYP), Asthma (ASMA), Chronic Bronchitis (CBRN), Emphysema (EMPH), Interstitial Lung Disease (ILD), Pulmonary Hypertension (PLHP), Benign Tumor/Cyst (BTC), Cystadenofibroma (CADF), Cystadenoma (CAD), Endometriosis (ENDO), Enlarged Ovaries (ENOV), Polycystic Ovaries (PCYS), Benign Prostatic Hyperplasia (BPH), Prostatic Intraepithelial Neoplasia (PIN), and Prostatitis (PRST).

PCan065 A10.3/B2.2 MAb ELISA Results

The concentration of PCan065 in serum from 594 healthy individuals, 726 individuals with cancer and 908 individuals with benign disease was determined with the PCan065 A10.3/B2.2 MAb ELISA. Of the 2228 samples tested, 92 samples (4%) were undetectable with the A10.3/B2.2 assay. These 92 samples are excluded in the analyses shown below, actual number of samples included is shown in Table 5.

Table 5 below shows the number of samples tested in each group of individuals, the minimum and maximum detected PCan065 concentration, the median PCan065 concentration, and the 25$^{th}$ and 75$^{th}$ percentile concentration of PCan065 in each group. Elevated levels of PCan065 were observed in individuals with breast, colon, lung, ovarian and prostate cancer.

TABLE 5

PCan065 Levels (ng/mL) in Normal and Cancer Samples (A10.3/B2.2 ELISA)

|  | NML F | NML M | BR CAN | CN CAN | LN CAN | OV CAN | PR CAN |
|---|---|---|---|---|---|---|---|
| Number of values | 274 | 291 | 145 | 122 | 191 | 97 | 152 |
| Minimum (ng/mL) | 0.115 | 0.018 | 0.016 | 0.061 | 0.016 | 0.021 | 0.017 |
| 25th Percentile (ng/mL) | 0.312 | 0.272 | 0.613 | 0.448 | 0.983 | 0.685 | 0.535 |
| Median (ng/mL) | 0.543 | 0.514 | 1.265 | 0.818 | 1.710 | 1.304 | 0.954 |
| 75th Percentile (ng/mL) | 0.895 | 0.748 | 1.784 | 1.409 | 3.007 | 2.059 | 1.686 |
| Maximum (ng/mL) | 3.733 | 1.885 | 17.170 | 10.060 | 10.690 | 13.820 | 6.853 |

The concentration of PCan065 was also measured in serum samples from individuals with various benign diseases with the PCan065 A10.3/B2.2 MAb ELISA. Tables 6A, 6B, 6C, 6D, 6E and 6F below show the number of samples tested in each group (listed above), the minimum and maximum detected PCan065 concentration, the median PCan065 concentration, and the $25^{th}$ and $75^{th}$ percentile concentration of PCan065 in each group.

TABLE 6A

PCan065 Levels (ng/mL) in Breast Cancer and Benign Samples (A10.3/B2.2 ELISA)

|  |  | BR CAN | | | BR BEN | | | |
|---|---|---|---|---|---|---|---|---|
|  | NRM F | All BR CAN | stage 1/2 | stage 3/4 | no stage info | All BR BEN | AHYP | FBAD | FBCY |
| Samples | 274 | 145 | 100 | 41 | 4 | 168 | 52 | 56 | 60 |
| Minimum | 0.115 | 0.016 | 0.016 | 0.228 | 0.242 | 0.021 | 0.178 | 0.110 | 0.021 |
| $25^{th}$ Percentile | 0.312 | 0.613 | 0.579 | 0.785 | 0.362 | 0.341 | 0.401 | 0.322 | 0.426 |
| Median | 0.543 | 1.265 | 1.224 | 1.433 | 0.542 | 0.795 | 0.809 | 0.703 | 0.902 |
| $75^{th}$ Percentile | 0.895 | 1.784 | 1.747 | 1.878 | 1.397 | 1.157 | 0.995 | 1.151 | 1.248 |
| Maximum | 3.733 | 17.170 | 17.170 | 7.572 | 2.193 | 6.583 | 1.995 | 3.719 | 6.583 |

TABLE 6B

PCan065 Levels (ng/mL) in Colon Cancer and Benign Samples (A10.3/B2.2 ELISA)

|  |  |  | CN CAN | | | CN BEN | | | |
|---|---|---|---|---|---|---|---|---|---|
|  | NRM F | NRM M | All CN CAN | stage 1/2 | stage 3/4 | All CN BEN | CHRN | PLYP | UCOL |
| Samples | 274 | 291 | 122 | 109 | 13 | 56 | 3 | 51 | 2 |
| Minimum | 0.115 | 0.018 | 0.061 | 0.061 | 0.492 | 0.113 | 0.248 | 0.113 | 0.876 |
| $25^h$ Percentile | 0.312 | 0.272 | 0.448 | 0.420 | 0.512 | 0.288 | n/a | 0.284 | n/a |
| Median | 0.543 | 0.514 | 0.818 | 0.802 | 1.008 | 0.514 | 0.463 | 0.510 | 0.993 |
| $75^{th}$ Percentile | 0.895 | 0.748 | 1.409 | 1.389 | 1.929 | 0.855 | n/a | 0.831 | n/a |
| Maximum | 3.733 | 1.885 | 10.060 | 10.060 | 6.453 | 4.762 | 1.166 | 4.762 | 1.109 |

TABLE 6C

PCan065 Levels (ng/mL) in Lung Cancer and Benign Samples (A10.3/B2.2 ELISA)

|  |  |  | LN CAN | | LN BEN | | | | |
|---|---|---|---|---|---|---|---|---|---|
|  | NRM F | NRM M | All LN CAN | stage 1/2 | stage 3/4 | All LN BEN | ASMA | CBRN | EMPH | ILD | PLHP |
| Samples | 274 | 291 | 191 | 74 | 117 | 239 | 46 | 47 | 49 | 48 | 49 |
| Minimum | 0.115 | 0.018 | 0.016 | 0.016 | 0.017 | 0.149 | 0.175 | 0.149 | 0.226 | 0.156 | 0.231 |
| $25^{th}$ Percentile | 0.312 | 0.272 | 0.983 | 0.882 | 1.101 | 0.775 | 0.659 | 0.653 | 0.736 | 0.761 | 1.291 |
| Median | 0.543 | 0.514 | 1.710 | 1.716 | 1.686 | 1.499 | 0.991 | 1.169 | 1.609 | 1.717 | 2.364 |
| $75^{th}$ Percentile | 0.895 | 0.748 | 3.007 | 2.987 | 3.064 | 2.456 | 1.790 | 2.038 | 2.151 | 3.008 | 4.256 |
| Maximum | 3.733 | 1.885 | 10.690 | 10.690 | 10.690 | 14.590 | 14.590 | 5.288 | 10.620 | 5.841 | 11.210 |

TABLE 7D

PCan065 Levels(ng/mL) in Ovarian Cancer and Benign Samples (A10.3/B2.2 ELISA)

|  | OV CAN | | | | OV BEN | | | | | | |
| --- | --- | --- | --- | --- | --- | --- | --- | --- | --- | --- | --- |
|  | NRM F | All OV CAN | stage 1/2 | stage 3/4 | All OV BEN | BTC | CADF | CAD | ENDO | ENOV | PCYS |
| Samples | 274 | 97 | 51 | 46 | 261 | 22 | 5 | 36 | 94 | 50 | 54 |
| Minimum | 0.115 | 0.021 | 0.222 | 0.021 | 0.027 | 0.178 | 0.323 | 0.156 | 0.027 | 0.093 | 0.035 |
| 25$^{th}$ Percentile | 0.312 | 0.685 | 0.486 | 0.854 | 0.231 | 0.474 | 0.360 | 0.276 | 0.192 | 0.183 | 0.185 |
| Median | 0.543 | 1.304 | 1.138 | 1.468 | 0.409 | 1.168 | 0.578 | 0.505 | 0.384 | 0.280 | 0.475 |
| 75$^{th}$ Percentile | 0.895 | 2.059 | 1.732 | 2.371 | 0.662 | 3.227 | 1.445 | 0.671 | 0.645 | 0.467 | 0.617 |
| Maximum | 3.733 | 13.820 | 13.820 | 5.943 | 12.630 | 11.030 | 2.124 | 1.132 | 12.630 | 6.658 | 5.619 |

TABLE 7E

PCan065 Levels(ng/mL) in Ovarian Cancer Subtypes (A10.3/B2.2 ELISA)

|  |  | Mucinous OV CAN | | | Serous OV CAN | | |
| --- | --- | --- | --- | --- | --- | --- | --- |
|  | NRM F | All Mucinous | stage 1/2 | stage 3/4 | All Serous | stage 1/2 | stage 3/4 |
| Samples | 274 | 31 | 19 | 12 | 66 | 32 | 34 |
| Minimum | 0.115 | 0.021 | 0.222 | 0.021 | 0.038 | 0.341 | 0.038 |
| 25th Percentile | 0.312 | 0.449 | 0.449 | 0.961 | 0.701 | 0.631 | 0.854 |
| Median | 0.543 | 1.299 | 1.119 | 2.014 | 1.317 | 1.213 | 1.418 |
| 75th Percentile | 0.895 | 2.098 | 1.438 | 2.873 | 2.136 | 1.767 | 2.303 |
| Maximum | 3.733 | 5.339 | 3.471 | 5.339 | 13.820 | 13.820 | 5.943 |

TABLE 7F

PCan065 Levels(ng/mL) in Prostate Cancer and Benign Samples (A10.3/B2.2 ELISA)

|  | PR CAN | | | | PR BEN | | | |
| --- | --- | --- | --- | --- | --- | --- | --- | --- |
|  | NRM M | All PR CAN | stage 1/2 | stage 3/4 | no stage info | All BR BEN | BPH | PIN | PRST |
| Samples | 291 | 152 | 112 | 37 | 3 | 140 | 62 | 10 | 68 |
| Minimum | 0.018 | 0.017 | 0.067 | 0.017 | 1.207 | 0.017 | 0.018 | 0.079 | 0.017 |
| 25$^{th}$ Percentile | 0.272 | 0.535 | 0.568 | 0.393 | n/a | 0.414 | 0.406 | 0.394 | 0.407 |
| Median | 0.514 | 0.954 | 0.952 | 0.937 | 1.779 | 0.901 | 0.943 | 1.356 | 0.784 |
| 75$^{th}$ Percentile | 0.748 | 1.686 | 1.697 | 1.603 | n/a | 1.421 | 1.842 | 1.748 | 1.207 |
| Maximum | 1.885 | 6.853 | 6.853 | 4.697 | 2.229 | 8.886 | 8.886 | 2.671 | 4.003 |

Elevated levels of PCan065 were observed in individuals with breast, colon, lung, ovarian, and prostate cancer. PCan065 was elevated in early stage (½) mucinous and serous ovarian cancer. PCan065 levels were not elevated significantly in individuals with breast, colon and ovarian benign conditions. These results demonstrate that elevated levels of PCan065 is indicative of an individual having breast, colon, lung, ovarian, or prostate cancer. Further, elevated levels of PCan065 are indicative early stage (stage ½) mucinous or serous ovarian cancer. Additionally, a PCan065 ELISA is able to determine PCan065 levels and discriminate individuals with breast, colon, lung, ovarian, and prostate cancers from individuals without disease and/or individuals with benign diseases.

Example 3

ROC Analysis of PCan065 Levels in Serum

The ability of a test or assay to discriminate diseased cases from normal cases is evaluated using Receiver Operating Characteristic (ROC) curve analysis (Metz, 1978; Zweig & Campbell, 1993). ROC curves can also be used to compare the diagnostic performance of two or more laboratory or diagnostic tests (Griner et al., 1981).

An ROC curve is generated by plotting the sensitivity against the specificity for each value. From the plot, the area under the curve (AUC) can be determined. The value for the area under the ROC curve (AUC) can be interpreted as follows: an area of 0.84, for example, means that a randomly selected positive result has a test value larger than that for a randomly chosen negative result 84% of the time (Zweig & Campbell, 1993). When the variable under study can not distinguish between two result groups, i.e. where there is no difference between the two distributions, the area will be equal to 0.5 (the ROC curve will coincide with the diagonal). When there is a perfect separation of the values of the two groups, i.e. there no overlapping of the distributions, the area under the ROC curve equals 1 (the ROC curve will reach the upper left corner of the plot).

The 95% confidence interval for the area can be used to test the hypothesis that the theoretical area is 0.5. If the confidence interval does not include the 0.5 value, then there is evidence that the laboratory test has the ability to distinguish between the two groups (Hanley & McNeil, 1982; Zweig & Campbell, 1993).

ROC Analysis of PCan065 A10.3/B2.2 MAb ELISA

PCan065 A10.3/B2.2 MAb ELISAs sensitivity and specificity for detecting cancer was calculated through receiver operating characteristic (ROC) analysis. Table 8 below shows the results of the Area Under the Curve (AUC) from the ROC analysis for PCan065 levels in case (cancer samples) versus controls (normal healthy samples and benign disease samples from the corresponding organ). AUC values were calculated using the PCan065 concentration levels described above with the A10.3/B2.2 MAb ELISA.

TABLE 8

PCan065 (A10.3/B2.2 MAb ELISA)
AUC Values for Various Cancers

|  | Cases (N) | Controls (N) | AUC | 95th Confidence Interval |
|---|---|---|---|---|
| Breast | 145 | 442 | 0.713 | 0.674 to 0.749 |
| Colon | 122 | 621 | 0.666 | 0.631 to 0.700 |
| Lung | 191 | 804 | 0.784 | 0.757 to 0.809 |
| Ovarian | 97 | 535 | 0.791 | 0.758 to 0.822 |
| Prostate | 152 | 431 | 0.679 | 0.639 to 0.716 |

ROC Analysis of PCan065 CA125

The sensitivity and specificity for PCan065 and CA125 alone or in combination to detect ovarian cancer was calculated through receiver operating characteristic (ROC) analysis. Table 9 below shows the results of the Area Under the Curve (AUC) from the ROC analysis for PCan065 and CA125 levels in cases (cancer samples) versus controls (normal healthy samples and benign disease samples from the corresponding organ) in all ovarian cancer samples, early stage (stage ½) samples and late stage (stage ¾) samples. AUC values were calculated using PCan065 levels described above and CA125 levels determined by Lumipulse from Fujirebio Inc. (Tokyo, Japan) in a set of the samples described above.

TABLE 9

PCan065 and CA125 AUC Values for Ovarian Cancer

|  | Cases (N) | Controls (N) | AUC | | |
|---|---|---|---|---|---|
|  |  |  | PCan065 | CA125 | PCan065 + CA125 |
| All Ovarian Cancer | 87 | 308 | 0.804 | 0.774 | 0.835 |
| Early Stage OvCa | 46 | 308 | 0.787 | 0.724 | 0.802 |
| Late Stage OvCa | 41 | 308 | 0.822 | 0.829 | 0.872 |

Results of PCan065 ROC Analyses

The results from the ROC analyses of the PCan065 ELISAs demonstrate that PCan065 alone is useful for detecting cancer. PCan065 performs better than the established marker CA125 for detection of ovarian cancer, specifically in detecting early stage (stage ½) cancers. Furthermore, PCan065 and CA125 in combination have a higher AUC for detecting ovarian cancers, including early stage, than either marker alone.

These results demonstrate PCan065, alone or in combination with other markers, is useful for detecting cancer, in particular ovarian cancer.

Example 4

Deposits

Deposit of Cell Lines and DNA

The following hybridoma cell lines were deposited with the American Type Culture Collection (ATCC) located at 10801 University Boulevard, Manassas, Va. 20110-2209, U.S.A., and accorded accession numbers.

TABLE 10

ATCC deposits

| Hybridoma | ATCC Accession No. | Deposit Date |
|---|---|---|
| PCan065.A10.3.2 |  |  |
| PCan065.B2.2.1 |  |  |

The names of the deposited hybridoma cell lines above may be shortened for convenience of reference. E.g. A10.3 corresponds to PCan065.A10.3. These hybridomas correspond to the clones (with their full names) listed in Table 10. Subclones of hybridomas are listed which have the same characteristics and properties of parental clones. Reference to a parent clone or hybridoma producing an anti-PCan065 antibody, such as PCan065.A10 or PCan065.B2, includes all subclones such as those listed in Table 10 above.

These deposits were made under the provisions of the Budapest Treaty on the International Recognition of the Deposit of Microorganisms for the Purpose of Patent Procedure and the Regulations there under (Budapest Treaty). This assures maintenance of viable cultures for 30 years from the date of deposit. The organisms will be made available by ATCC under the terms of the Budapest Treaty, and subject to an agreement between diaDexus, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 3 7 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention

We claim:

1. A method for detecting the presence of ovarian cancer in a subject comprising:
   (a) determining the level of PCan065 in a sample from the subject, and
   (b) comparing the level of PCan065 determined in step (a) to the level of PCan065 in a control sample, wherein an increase in the level of PCan065 in the sample from the subject as compared to the control is indicative of the presence of ovarian cancer.

2. The method of claim 1 wherein the sample is selected from the group consisting of cells, tissues and bodily fluids.

3. The method of claim 2 where in the bodily fluid is selected from the group consisting of blood, serum, plasma, urine, ascites, peritoneal wash, saliva, sputum, seminal fluids, tears, mucous membrane secretions, and other bodily excretions such as stool.

4. The method of claim 1 wherein the control sample is from a subject without a cancer overexpressing PCan065.

5. The method of claim 1 wherein the control is a sample of known concentration of PCan065.

6. The method of claim 1 wherein the level of PCan065 in a sample from the subject is determined by binding of an antibody which binds specifically to PCan065 or a PCan065 peptide.

7. The method of claim 6 wherein the antibody is a monoclonal antibody, an antibody fragment, a chimeric or a humanized antibody.

8. The method of claim 6 wherein the antibody is detectably labeled.

9. Immediately following the word "PCan065 in the fifth line the text ", wherein PCan065 comprises the amino acid sequence of SEQ ID NO:5" has been added.

10. Immediately following the word "PCan065 in the fifth line the text ", wherein PCan065 comprises the amino acid sequence of SEQ ID NO:5" has been added.

11. The method of claim 6 wherein the antibody specifically binds a PCan065 peptide containing a post translational modification, motif, or domain.

12. The method of claim 11 wherein the post translational modification, motif, or domain is a transforming growth factor-beta (TGF-beta) domain, N-glycosylation site, or proteolytic cleavage site.

13. The method of claim 6 wherein the antibody competes for binding with a molecule that binds a transforming growth factor-beta (TGF-beta) domain.

14. The method of claim 6 wherein the antibody is produced by bacterial, insect, or mammalian cells.

* * * * *

SEQUENCE LISTING

```
<160> NUMBER OF SEQ ID NOS: 5

<210> SEQ ID NO 1
<211> LENGTH: 143
<212> TYPE: PRT
```

<213> ORGANISM: Artificial sequence
<220> FEATURE:
<223> OTHER INFORMATION: Synthetic

<400> SEQUENCE: 1

```
Met Leu Gln Asn Ser Ala Val Leu Leu Val Val Ile Ser Ala Ser
1               5                   10                  15

Ala Asp Ile Ala Arg Asn Gly Asp His Cys Pro Leu Gly Pro Gly Arg
            20                  25                  30

Cys Cys Arg Leu His Thr Val Arg Ala Ser Leu Glu Asp Leu Gly Trp
        35                  40                  45

Ala Asp Trp Val Leu Ser Pro Arg Glu Val Gln Val Thr Met Cys Ile
    50                  55                  60

Gly Ala Cys Pro Ser Gln Phe Arg Ala Ala Asn Met His Ala Gln Ile
65                  70                  75                  80

Lys Thr Ser Leu His Arg Leu Lys Pro Asp Thr Val Pro Ala Pro Cys
                85                  90                  95

Cys Val Pro Ala Ser Tyr Asn Pro Met Val Leu Ile Gln Lys Thr Asp
            100                 105                 110

Thr Gly Val Ser Leu Gln Thr Tyr Asp Asp Leu Leu Ala Lys Asp Cys
        115                 120                 125

His Cys Ile Ala Ser His His His His His His His His
    130                 135                 140
```

<210> SEQ ID NO 2
<211> LENGTH: 320
<212> TYPE: PRT
<213> ORGANISM: ARTIFICIAL SEQUENCE
<220> FEATURE:
<223> OTHER INFORMATION: Synthetic

<400> SEQUENCE: 2

```
Met Pro Gly Gln Glu Leu Arg Thr Leu Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
```

```
                195                 200                 205
Arg Cys Cys Arg Leu His Thr Val Arg Ala Ser Leu Glu Asp Leu Gly
210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Asn Met His Ala Gln
                245                 250                 255

Ile Lys Thr Ser Leu His Arg Leu Lys Pro Asp Thr Val Pro Ala Pro
                260                 265                 270

Cys Cys Val Pro Ala Ser Tyr Asn Pro Met Val Leu Ile Gln Lys Thr
                275                 280                 285

Asp Thr Gly Val Ser Leu Gln Thr Tyr Asp Asp Leu Leu Ala Lys Asp
                290                 295                 300

Cys His Cys Ile Ala Ser His His His His His His His His
305                 310                 315                 320
```

<210> SEQ ID NO 3
<211> LENGTH: 799
<212> TYPE: PRT
<213> ORGANISM: ARTIFICIAL SEQUENCE
<220> FEATURE:
<223> OTHER INFORMATION: Synthetic

<400> SEQUENCE: 3

```
Met Ser Gly Gly His Gln Leu Gln Leu Ala Ala Leu Trp Pro Trp Leu
1               5                   10                  15

Leu Met Ala Thr Leu Gln Ala Gly Phe Gly Arg Thr Gly Leu Val Leu
                20                  25                  30

Ala Ala Ala Val Glu Ser Glu Arg Ser Ala Glu Gln Lys Ala Ile Ile
                35                  40                  45

Arg Val Ile Pro Leu Lys Met Asp Pro Thr Gly Lys Leu Asn Leu Thr
50                  55                  60

Leu Glu Gly Val Phe Ala Gly Val Ala Glu Ile Thr Pro Ala Glu Gly
65                  70                  75                  80

Lys Leu Met Gln Ser His Pro Leu Tyr Leu Cys Asn Ala Ser Asp Asp
                85                  90                  95

Asp Asn Leu Glu Pro Gly Phe Ile Ser Ile Val Lys Leu Glu Ser Pro
                100                 105                 110

Arg Arg Ala Pro Arg Pro Cys Leu Ser Leu Ala Ser Lys Ala Arg Met
                115                 120                 125

Ala Gly Glu Arg Gly Ala Ser Ala Val Leu Phe Asp Ile Thr Glu Asp
                130                 135                 140

Arg Ala Ala Ala Glu Gln Leu Gln Gln Pro Leu Gly Leu Thr Trp Pro
145                 150                 155                 160

Val Val Leu Ile Trp Gly Asn Asp Ala Glu Lys Leu Met Glu Phe Val
                165                 170                 175

Tyr Lys Asn Gln Lys Ala His Val Arg Ile Glu Leu Lys Glu Pro Pro
                180                 185                 190

Ala Trp Pro Asp Tyr Asp Val Trp Ile Leu Met Thr Val Val Gly Thr
                195                 200                 205

Ile Phe Val Ile Ile Leu Ala Ser Val Leu Arg Ile Arg Cys Arg Pro
                210                 215                 220

Arg His Ser Arg Pro Asp Pro Leu Gln Gln Arg Thr Ala Trp Ala Ile
225                 230                 235                 240

Ser Gln Leu Ala Thr Arg Arg Tyr Gln Ala Ser Cys Arg Gln Ala Arg
                245                 250                 255
```

```
Gly Glu Trp Pro Asp Ser Gly Ser Ser Cys Ser Ser Ala Pro Val Cys
            260                 265                 270

Ala Ile Cys Leu Glu Glu Phe Ser Glu Gly Gln Glu Leu Arg Val Ile
            275                 280                 285

Ser Cys Leu His Glu Phe His Arg Asn Cys Val Asp Pro Trp Leu His
            290                 295                 300

Gln His Arg Thr Cys Pro Leu Cys Met Phe Asn Ile Thr Glu Gly Asp
305                 310                 315                 320

Ser Phe Ser Gln Ser Leu Gly Pro Ser Arg Ser Tyr Gln Glu Pro Gly
            325                 330                 335

Arg Arg Leu His Leu Ile Arg Gln His Pro Gly His Ala His Tyr His
            340                 345                 350

Leu Pro Ala Ala Tyr Leu Leu Gly Pro Ser Arg Ser Ala Val Ala Arg
            355                 360                 365

Pro Pro Arg Pro Gly Pro Phe Leu Pro Ser Gln Glu Pro Gly Met Gly
            370                 375                 380

Pro Arg His His Arg Phe Pro Arg Ala Ala His Pro Arg Ala Pro Gly
385                 390                 395                 400

Glu Gln Gln Arg Leu Ala Gly Ala Gln His Pro Tyr Ala Gln Gly Trp
            405                 410                 415

Gly Leu Ser His Leu Gln Ser Thr Ser Gln His Pro Ala Ala Cys Pro
            420                 425                 430

Val Pro Leu Arg Arg Ala Arg Pro Pro Asp Ser Ser Gly Ser Gly Glu
            435                 440                 445

Ser Tyr Cys Thr Glu Arg Ser Gly Tyr Leu Ala Asp Gly Pro Ala Ser
            450                 455                 460

Asp Ser Ser Ser Gly Pro Cys His Gly Ser Ser Asp Ser Val Val
465                 470                 475                 480

Asn Cys Thr Asp Ile Ser Leu Gln Gly Val His Gly Ser Ser Ser Thr
            485                 490                 495

Phe Cys Ser Ser Leu Ser Ser Asp Phe Asp Pro Leu Val Tyr Cys Ser
            500                 505                 510

Pro Lys Gly Asp Pro Gln Arg Val Asp Met Gln Pro Ser Val Thr Ser
            515                 520                 525

Arg Pro Arg Ser Leu Asp Ser Val Val Pro Thr Gly Glu Thr Gln Val
            530                 535                 540

Ser Ser His Val His Tyr His Arg His Arg His His Tyr Lys Lys
545                 550                 555                 560

Arg Phe Gln Trp His Gly Arg Lys Pro Gly Pro Glu Thr Gly Val Pro
            565                 570                 575

Gln Ser Arg Pro Pro Ile Pro Arg Thr Gln Pro Gln Pro Glu Pro Pro
            580                 585                 590

Ser Pro Asp Gln Gln Val Thr Arg Ser Asn Ser Ala Ala Pro Ser Gly
            595                 600                 605

Arg Leu Ser Asn Pro Gln Cys Pro Arg Ala Leu Pro Glu Pro Ala Pro
            610                 615                 620

Gly Pro Val Asp Ala Ser Ser Ile Cys Pro Ser Thr Ser Ser Leu Phe
625                 630                 635                 640

Asn Leu Gln Lys Ser Ser Leu Ser Ala Arg His Pro Gln Arg Lys Arg
            645                 650                 655

Arg Gly Gly Pro Ser Glu Pro Thr Pro Gly Ser Arg Pro Gln Asp Ala
            660                 665                 670

Thr Val His Pro Ala Cys Gln Ile Phe Pro His Tyr Thr Pro Ser Val
```

-continued

```
                675                 680                 685
Ala Tyr Pro Trp Ser Pro Glu Ala His Pro Leu Ile Cys Gly Pro Pro
        690                 695                 700

Gly Leu Asp Lys Arg Leu Leu Pro Glu Thr Pro Gly Pro Cys Tyr Ser
705                 710                 715                 720

Asn Ser Gln Pro Val Trp Leu Cys Leu Thr Pro Arg Gln Pro Leu Glu
                725                 730                 735

Pro His Pro Pro Gly Glu Gly Pro Ser Glu Trp Ser Ser Asp Thr Ala
            740                 745                 750

Glu Gly Arg Pro Cys Pro Tyr Pro His Cys Gln Val Leu Ser Ala Gln
                755                 760                 765

Pro Gly Ser Glu Glu Glu Leu Glu Glu Leu Cys Glu Gln Ala Val Met
        770                 775                 780

His Asp Ile Ala Ser His His His His His His His His
785                 790                 795

<210> SEQ ID NO 4
<211> LENGTH: 175
<212> TYPE: PRT
<213> ORGANISM: ARTIFICIAL SEQUENCE
<220> FEATURE:
<223> OTHER INFORMATION: Synthetic

<400> SEQUENCE: 4

Met Leu Gln Asn Ser Ala Val Leu Leu Val Leu Val Ile Ser Ala Ser
1               5                   10                  15

Ala Thr His Glu Ala Glu Gln Ser Arg Met His Asp Ile Ile Met Arg
            20                  25                  30

Pro Ser Cys Ala Pro Gly Trp Phe Tyr His Lys Ser Asn Cys Tyr Gly
        35                  40                  45

Tyr Phe Arg Lys Leu Arg Asn Trp Ser Asp Ala Glu Leu Glu Cys Gln
    50                  55                  60

Ser Tyr Gly Asn Gly Ala His Leu Ala Ser Ile Leu Ser Leu Lys Glu
65                  70                  75                  80

Ala Ser Thr Ile Ala Glu Tyr Ile Ser Gly Tyr Gln Arg Ser Gln Pro
                85                  90                  95

Ile Trp Ile Gly Leu His Asp Pro Gln Lys Arg Gln Gln Trp Gln Trp
            100                 105                 110

Ile Asp Gly Ala Met Tyr Leu Tyr Arg Ser Trp Ser Gly Lys Ser Met
        115                 120                 125

Gly Gly Asn Lys His Cys Ala Glu Met Ser Ser Asn Asn Asn Phe Leu
    130                 135                 140

Thr Trp Ser Ser Asn Glu Cys Asn Lys Arg Gln His Phe Leu Cys Lys
145                 150                 155                 160

Tyr Arg Pro Ala Ser His His His His His His His His His
                165                 170                 175

<210> SEQ ID NO 5
<211> LENGTH: 308
<212> TYPE: PRT
<213> ORGANISM: Homo sapiens
<220> FEATURE:
<221> NAME/KEY: VARIANT
<222> LOCATION: (9)..(9)
<223> OTHER INFORMATION: Xaa = Leu or Val
<220> FEATURE:
<221> NAME/KEY: VARIANT
<222> LOCATION: (48)..(48)
<223> OTHER INFORMATION: Xaa = Thr or Ser
<220> FEATURE:
```

```
<221> NAME/KEY: VARIANT
<222> LOCATION: (202)..(202)
<223> OTHER INFORMATION: Xaa = Asp or His
<220> FEATURE:
<221> NAME/KEY: VARIANT
<222> LOCATION: (249)..(249)
<223> OTHER INFORMATION: Xaa = Gly or Arg
<220> FEATURE:
<221> NAME/KEY: VARIANT
<222> LOCATION: (272)..(272)
<223> OTHER INFORMATION: Xaa = His or Pro

<400> SEQUENCE: 5

Met Pro Gly Gln Glu Leu Arg Thr Xaa Asn Gly Ser Gln Met Leu Leu
1               5                   10                  15

Val Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Xaa
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp Xaa Cys Pro Leu Gly Pro Gly
            195                 200                 205

Arg Cys Cys Arg Leu His Thr Val Arg Ala Ser Leu Glu Asp Leu Gly
210                 215                 220

Trp Ala Asp Trp Val Leu Ser Pro Arg Glu Val Gln Val Thr Met Cys
225                 230                 235                 240

Ile Gly Ala Cys Pro Ser Gln Phe Xaa Ala Ala Asn Met His Ala Gln
                245                 250                 255

Ile Lys Thr Ser Leu His Arg Leu Lys Pro Asp Thr Val Pro Ala Xaa
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305
```